United States Patent
Pisarenco et al.

(10) Patent No.: US 10,146,140 B2
(45) Date of Patent: Dec. 4, 2018

(54) METHODS AND APPARATUS FOR SIMULATING INTERACTION OF RADIATION WITH STRUCTURES, METROLOGY METHODS AND APPARATUS, DEVICE MANUFACTURING METHOD

(71) Applicant: ASML Netherlands B.V., Veldhoven (NL)

(72) Inventors: Maxim Pisarenco, Son en Breugel (NL); Richard Quintanilha, Eindhoven (NL); Markus Gerardus Martinus Maria Van Kraaij, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 12 days.

(21) Appl. No.: 15/285,051

(22) Filed: Oct. 4, 2016

(65) Prior Publication Data

US 2017/0102623 A1  Apr. 13, 2017

(30) Foreign Application Priority Data

Oct. 12, 2015  (EP) .................................... 15189343

(51) Int. Cl.
*G03B 27/68* (2006.01)
*G03F 7/20* (2006.01)
(Continued)

(52) U.S. Cl.
CPC ......... *G03F 7/70625* (2013.01); *G01B 15/00* (2013.01); *G01N 23/201* (2013.01); *G03F 7/705* (2013.01); *G01N 2223/501* (2013.01)

(58) Field of Classification Search
CPC ............. G01B 15/00; G01N 2223/501; G01N 23/201; G03F 7/70625; G03F 7/705
See application file for complete search history.

(56) References Cited

U.S. PATENT DOCUMENTS

| | | | | |
|---|---|---|---|---|
| 5,363,050 A | * | 11/1994 | Guo | G01N 22/00 324/638 |
| 5,963,329 A | * | 10/1999 | Conrad | G01B 11/02 356/601 |

(Continued)

FOREIGN PATENT DOCUMENTS

| | | |
|---|---|---|
| WO | WO 2007/044827 A2 | 4/2007 |
| WO | WO 2015/032586 A1 | 3/2015 |

(Continued)

OTHER PUBLICATIONS

Wang et al., "Validity criterion for the Born approximation convergence in microscopy imaging: comment," Journal of the Optical Society of America A, vol. 28, No. 4, Apr. 2011, pp. 662-664.

(Continued)

*Primary Examiner* — Deoram Persaud
(74) *Attorney, Agent, or Firm* — Sterne, Kessler, Goldstein & Fox P.L.L.C.

(57) ABSTRACT

A structure of interest is irradiated with radiation for example in the x-ray or EUV waveband, and scattered radiation is detected by a detector (306). A processor (308) calculates a property such as linewidth (CD) by simulating interaction of radiation with a structure and comparing the simulated interaction with the detected radiation. A layered structure model (600, 610) is used to represent the structure in a numerical method. The structure model defines for each layer of the structure a homogeneous background permittivity and for at least one layer a non-homogeneous contrast permittivity. The method uses Maxwell's equation in Born approximation, whereby a product of the contrast permittivity and the total field is approximated by a product of the contrast permittivity and the background field. A computation complexity is reduced by several orders of magnitude compared with known methods.

13 Claims, 8 Drawing Sheets

(51) Int. Cl.
  *G01B 15/00* (2006.01)
  *G01N 23/201* (2018.01)

(56) References Cited

U.S. PATENT DOCUMENTS

| | | | |
|---|---|---|---|
| 6,658,144 B1 | 12/2003 | Hatab | |
| 2002/0033954 A1* | 3/2002 | Niu | G01B 11/0675 356/601 |
| 2004/0078173 A1* | 4/2004 | Bischoff | G01N 21/4788 703/2 |
| 2005/0137809 A1 | 6/2005 | Chang et al. | |
| 2005/0275850 A1* | 12/2005 | Bischoff | G01B 11/24 356/600 |
| 2008/0041306 A1* | 2/2008 | Itagaki | C23C 16/4404 118/665 |
| 2009/0138246 A1* | 5/2009 | Chow | G06F 17/5018 703/2 |
| 2011/0018400 A1* | 1/2011 | Kato | C08F 297/02 310/363 |
| 2011/0098992 A1* | 4/2011 | Van Beurden | G03F 7/705 703/2 |
| 2011/0218789 A1* | 9/2011 | Van Beurden | G03F 7/705 703/13 |
| 2012/0123748 A1* | 5/2012 | Aben | G03F 7/70483 703/2 |
| 2012/0168607 A1* | 7/2012 | Okhmatovski | A61B 5/0507 250/206 |
| 2013/0018585 A1 | 1/2013 | Zhdanov et al. | |
| 2013/0035911 A1* | 2/2013 | Pisarenco | G03F 7/705 703/2 |
| 2013/0066597 A1 | 3/2013 | Van Beurden | |
| 2013/0135136 A1* | 5/2013 | Haynes | G01S 13/89 342/22 |
| 2013/0144560 A1 | 6/2013 | Pisarenco et al. | |
| 2013/0271740 A1* | 10/2013 | Quintanilha | G03F 1/144 355/67 |
| 2014/0222380 A1* | 8/2014 | Kuznetsov | G01N 21/4788 702/189 |
| 2014/0325827 A1 | 11/2014 | Lipson et al. | |
| 2015/0142397 A1* | 5/2015 | Pond | G06F 17/5009 703/2 |
| 2015/0331336 A1* | 11/2015 | Quintanilha | G03F 7/70683 355/77 |
| 2016/0161627 A1* | 6/2016 | Khalaj Amineh | E21B 47/0006 702/6 |
| 2016/0223476 A1* | 8/2016 | Quintanilha | G03F 7/70591 |
| 2016/0223916 A1* | 8/2016 | Van Beurden | G03F 7/705 |
| 2016/0273906 A1* | 9/2016 | Pisarenco | G03F 7/705 |
| 2016/0282282 A1* | 9/2016 | Quintanilha | G01N 21/8806 |
| 2016/0320711 A1* | 11/2016 | Quintanilha | G03F 7/70625 |
| 2016/0377990 A1* | 12/2016 | Quintanilha | G01N 21/95623 355/67 |
| 2017/0017738 A1* | 1/2017 | Dirks | G06F 17/5009 |
| 2017/0045823 A1* | 2/2017 | Quintanilha | G03F 1/24 |
| 2017/0184981 A1* | 6/2017 | Quintanilha | G03F 7/70625 |
| 2017/0345138 A1* | 11/2017 | Middlebrooks | G06T 7/001 |
| 2017/0357155 A1* | 12/2017 | Quintanilha | G03F 7/70633 |

FOREIGN PATENT DOCUMENTS

| | | |
|---|---|---|
| WO | WO 2015/078670 A1 | 6/2015 |
| WO | WO 2015/172963 A1 | 11/2015 |

OTHER PUBLICATIONS

International Search Report and Written Opinion of the International Searching Authority directed to related International Patent Application No. PCT/EP2016/072500, dated Mar. 24, 2017; 16 pages.

Pisarenco et al., "Fast semi-analytical solution of Maxwell's equations in Born approximation for periodic structures," Journal of the Optical Society of America A, vol. 33, No. 4, Nov. 4, 2015; pp. 610-617.

Lalanne et al., "A microscopic view of the electromagnetic properties of sub-γ metallic surfaces," Surface Science Reports, vol. 64, No. 10, 2009; 37 pages.

Boulenguez et al., "Multiple scaled disorder in the photonic structure of *Morph rhetenor* butterfly," Applied Physics A, vol. 105, Jan. 7, 2012; pp. 1005-1011.

Pisarenco et al., "Aperiodic Fourier modal method in contrast-field formulation for simulation of scattering from finite structures," Journal of the Optical Society of America A, vol. 27, No. 11, Nov. 2010; pp. 2423-2431.

Lemaillet et al., "Intercomparison between optical and x-ray scatterometry measurements of FinFET structures," Institute for Research in Electronics and Applied Physics, Proceedings of SPIE, vol. 8681, 2013; 8 pages.

Jones et al., "Small angle x-ray scattering for sub-100 nm pattern characterization," Applied Physics Letters, vol. 83, No. 19, Nov. 10, 2003; pp. 4059-4061.

Li et al., "On the Validity of Born Approximation," Progress in Electromagnetics Research, vol. 107, 2010; pp. 219-237.

Sinha et al., " X-ray and neutron scattering from rough surfaces," Corporate Research Science Laboratory, Exxon Research and Engineering Company, Physical. Review B, vol. 38, No. 4, Aug. 1, 1988; pp. 2297-2311.

Van Den Berg P. M., "Iterative Computational Techniques in Scattering Based Upon the Integrated Square Error Criterion," IEEE Trnasactions on Antennas and Propagation, vol. AP-32, No. 10, Oct. 1984; pp. 1063-1071.

Trattner et al., "Validity criterion for the Born approximation convergence in microscopy imaging," Journal of the Optical Society of America A, vol. 26, No. 5., May 2009; pp. 1147-1156.

Pisarenco et al., "Modified S-matrix algorithm for the aperiodic Fourier modal method in contrast-field formulation," Journal of the Optical Society of America A, vol. 28, No. 7, Jul. 2011; pp. 1364-1371.

Wikipedia Contributors, "Galerkin Method," Wikipedia, the free encyclopedia, 2015, https://en.wikipedia.org/wiki/Galerkin_method; 4 pages.

Wikipedia Contributors, "Kronecker delta," Wikipedia, the free encyclopedia, 2015, https://en.wikipedia.org/wiki/Kronecker_delta; 6 pages.

Wikipedia Contributors, "Refractive index," Wikipedia, the free encyclopedia, 2015, https://en.wikipedia.org/wiki/Refractive_index; 15 pages.

Wikipedia Contributors, "Toeplitz matrix," Wikipedia, the free encyclopedia, 2015, https://en.wikipedia.org/wiki/Toeplitz_matrix; 4 pages.

Yeh P., "Optical Waves in Layered Media," Wiley Series in Pure and Applied Optics, Wiley-Interscience, 2nd edition, Chapter 5, "Matrix Formulation for Isotropic Layered Media," 2005; pp. 102-117.

\* cited by examiner

METHODS AND APPARATUS FOR SIMULATING INTERACTION OF RADIATION WITH STRUCTURES, METROLOGY METHODS AND APPARATUS, DEVICE MANUFACTURING METHOD

FIELD

The present invention relates to methods and apparatus for simulating interaction of radiation with structures. The invention may be applied for example in metrology of microscopic structures, for example to assess and improve performance of a lithographic, or to determine the structure of a molecule or crystal. The radiation may be electromagnetic radiation of any desired wavelength, but the invention may find particular application in x-ray and so-called soft x-ray (extreme ultraviolet) wavebands.

BACKGROUND

While the invention may be applied to a range of applications, consider as an example the manufacture of integrated circuits (ICs) by a lithographic process. In that instance, a lithographic apparatus is used to apply a pattern of device features to be formed on an individual layer of the IC. This pattern can be transferred onto a target portion (e.g., including part of, one, or several dies) on a substrate (e.g., a silicon wafer).

In lithographic processes, it is desirable frequently to make measurements of the structures created, e.g., for process control and verification. Various tools for making such measurements are known, including scanning electron microscopes (SEM), which are often used to measure critical dimension (CD). Other specialized tools are used to measure parameters related to asymmetry. One of these parameters is overlay, the accuracy of alignment of two layers in a device. Recently, various forms of scatterometers have been developed for use in the lithographic field. These devices direct a beam of radiation onto a target and measure one or more properties of the scattered radiation as it is reflected and/or transmitted by the target, e.g., intensity at a single angle as a function of wavelength; intensity at one or more wavelengths as a function of angle; or polarization as a function of angle—to obtain a "spectrum" of one form or another. The term "spectrum" in this context will be used with a wide scope. It may refer to a spectrum of different wavelengths (colors), it may refer to a spectrum of different directions (diffraction angles), different polarizations, or a combination of any or all of these. From this spectrum a property of interest of the target can be determined. Determination of the property of interest may be performed by various techniques. One particular approach is to perform reconstruction of the target structure by iterative calculations. A mathematical model of the target is created and calculations are performed to simulate interaction of radiation with the target. Parameters of the model are adjusted and calculations repeated until the simulated spectrum becomes the same as the observed spectrum. The adjusted parameter values then serve as a measurement of the real target structure. Each updated model represents a point in "parameter space", which is a mathematical space with as many dimensions as there are parameters in the model. The aim of the iterative process is to converge to a point in parameter space that represents, at least approximately, the parameters of the actual target structure. In another approach, simulated spectra are calculated in advance for a variety of points in the parameter space. These simulated spectra serve as a "library" which is searched to find a match for a spectrum observed later on a real target.

Compared with SEM techniques, scatterometers can be used with much higher throughput, on a large proportion or even all of the product units. The measurements can be performed very quickly. On the other hand, reconstruction requires a great deal of computation. For example, in many applications, the FMM method in one-dimensional models requires a calculation of order $N^3$ (N cubed) operations, for a given number N of harmonics. (In two-dimensional models the calculation is of order $Nx^3*Ny^3$.) As the sizes of features produced by lithography shrink ever smaller and dimensional tolerances shrink accordingly, there is an interest in the use of diffraction based techniques (scatterometry) at shorter wavelengths, such as x-ray and "soft x-ray" (extreme ultraviolet) wavelengths. Scattering of electromagnetic waves can be simulated by use of Maxwell's equations at such short wavelengths in the same way as at longer wavelengths. This approach is used to analyze x-ray diffraction patterns from all field of physics: power diffraction, crystallography, biology, etc. In semiconductor manufacturing, reconstruction of critical dimension using small-angle x-ray scattering (CD-SAXS) is already known. Examples are in references (1) (Lemaillet 2013) and (2)(Jones 2003).

Examples of transmissive and reflective metrology techniques using these wavelengths in transmissive and/or reflective scattering modes are disclosed in pending patent applications PCT/EP2015/058238 filed 16 Apr. 2015, EP15180807.8 filed 12 Aug. 2015 and EP15180740.1 filed 12 Aug. 2015, not published at the present priority date.

In the x-ray and EUV range of the electromagnetic spectrum, many materials become quite transparent. In other words, the contrast between the materials in the patterned layer is small. (The patterned may be made of two or more solid materials, or there may be a pattern in one material in an atmosphere, such as air, vacuum or He, as is known in the x-ray and EUV fields. In this regime, a technique known as the Born approximation has been used in the References (3) (Li 2010) and (4) (Sinha 1988) to simplify the model and its numerical solution. Non-patent references are listed in full at the end of this description. In this case a scattered radiation term in the Maxwell equations, which is defined as the product of the contrast permittivity and the total field, is approximated by the product of the contrast permittivity and the background (or incident) field. In the references, the Born approximation is typically implemented through integral methods (see for example References (5) (Van den Berg 1984) and (6) (Trattner 2009).

In order to find the numerical solution of the integral formulation of the Born approximation, a full discretization (in all spatial dimensions x, y, z) is required. In typical applications, the domain size (that is, the spatial period of the model structure, or other spatial extent) is much larger than the wavelength. For example, the spatial period of a target grating might be ten or so nanometers while the radiation wavelength is a fraction of a nanometer. If we denote by sx/sy/sz the ratio between domain size in the x/y/z direction and the wavelength of radiation used, then the number of degrees of freedom (the number of unknowns in the discretized Maxwell's equations) is proportional to $sx*sy*sz$. Since this product can easily reach a factor of 1000, the computation might become expensive. Moreover, due to discretization in the z direction, the solution in the known integral methods is prone to approximation errors in all directions.

As an alternative to integral methods for simulating interaction of radiation with different structures, modal methods are also known, where the radiation field and the structure are transformed into a mode space. An example of a modal method is the Fourier modal method (FMM) or rigorous coupled wave analysis or RCWA. RCWA is well-known and suitable for application to periodic structures, especially. Modes in the Fourier modal method are also referred to as "harmonics". Techniques for extending the application of FMM to aperiodic structures (including "finite periodic" structures), are described in Reference (7) M Pisarenco and others, "Aperiodic Fourier modal method in contrast-field formulation for simulation of scattering from finite structures", J. Opt. Soc. Am. A, Vol. 27, No. 11 (November 2010), pp 2423-2431. A further paper on this topic by the same authors is (8) "Modified S-matrix algorithm for the aperiodic Fourier modal method in contrast-field formulation", J. Opt. Soc. Am. A 28, 1364-1371 (2011). The contents of both papers are hereby incorporated by reference. According to these references, complexity in the calculations is reduced by considering separately a background permittivity and a contrast permittivity, and calculating a background radiation field and a scattered radiation field. Representing each of these fields in Fourier space allows an analytical solution of Maxwell's equations in one dimension.

SUMMARY OF THE INVENTION

The invention aims to allow simulation of interactions of radiation with microscopic structures by a more economical and/or robust method. The inventors have recognized that a new formulation of a modal method such as FMM (RCWA) can be devised, which is adapted to allow a fast, semi-analytical solution of Maxwell's equations in a Born approximation. The complexity of calculations can be significantly reduced in some valuable applications. The techniques disclosed herein are in no way limited to any specific form of modal method, nor to periodic or aperiodic structures.

The invention in a first aspect provides a method of simulating interaction of radiation with a structure, the method including the steps of:

(a) defining a layered structure model to represent the structure in a two- or three-dimensional model space, the structure model defining for each layer of the structure a homogeneous background permittivity and for at least one layer a non-homogeneous contrast permittivity; and (b) using the structure model in a modal method to simulate interaction of radiation with the structure, a total field being calculated in terms of a background field and a contrast field, the background field within each layer being independent of the contrast permittivity.

wherein step (b) uses Maxwell's equation in a Born approximation, whereby a product of the contrast permittivity and the total field is approximated by a product of the contrast permittivity and the background field.

The method can be used as part of a metrology method, using the simulated interactions for reconstruction of the structure. The simulation of interactions can be performed for example as an iterative process, comparing the results of each iteration with an interaction already observed on the structure under investigation. The iterative process converges to a point in parameter space that serves as a measurement of the observed structure. The simulation of interactions can alternatively be performed in advance of the observations, for example to generate a library of simulated results for many different points in the parameter space. A measurement of a structure under investigation is then obtained by comparing an observed interaction with the simulated interactions in the library, and identifying a best match. The simulation of interactions need not be complete or explicit. For example, the simulation of interactions can be performed in a differential mode, simulating the influence of a change of structure, rather than the whole structure.

The invention in a second aspect provides a processing apparatus for use in simulating interaction of radiation with a structure, the processing apparatus comprising:

storage for a layered structure model to represent the structure in a two- or three-dimensional model space, the structure model defining for each layer of the structure a homogeneous background permittivity and for at least one layer a non-homogeneous contrast permittivity; and a processor for using the structure model in a modal method to simulate interaction of radiation with the structure, a total field being calculated in terms of a background field and a contrast field, the background field within each layer being independent of the contrast permittivity.

wherein the processor is arranged to use Maxwell's equation in a Born approximation, whereby a product of the contrast permittivity and the total field is approximated by a product of the contrast permittivity and the background field.

The invention in a third aspect provides metrology apparatus for use in determining parameters of a structure, the metrology apparatus comprising:

an irradiation system for generating a beam of radiation;

a substrate support operable with the irradiation system for irradiating a structure formed on the substrate with radiation;

a detection system for detecting radiation after interaction with the structure; and a processing apparatus according to the second aspect of the invention as set forth above, arranged to simulate interaction of radiation with the structure and to compare the detected radiation with a result of the simulated interaction.

The processing apparatus may be provided for performing the method according to the invention as set forth above. The processing apparatus and/or method may be implemented by running a suitable program of instructions on a computer. The instructions may form a computer program product. The instructions may be stored in a non-transitory storage medium.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

Embodiments of the invention will now be described, by way of example, with reference to the accompanying drawings in which.

Figure 4:
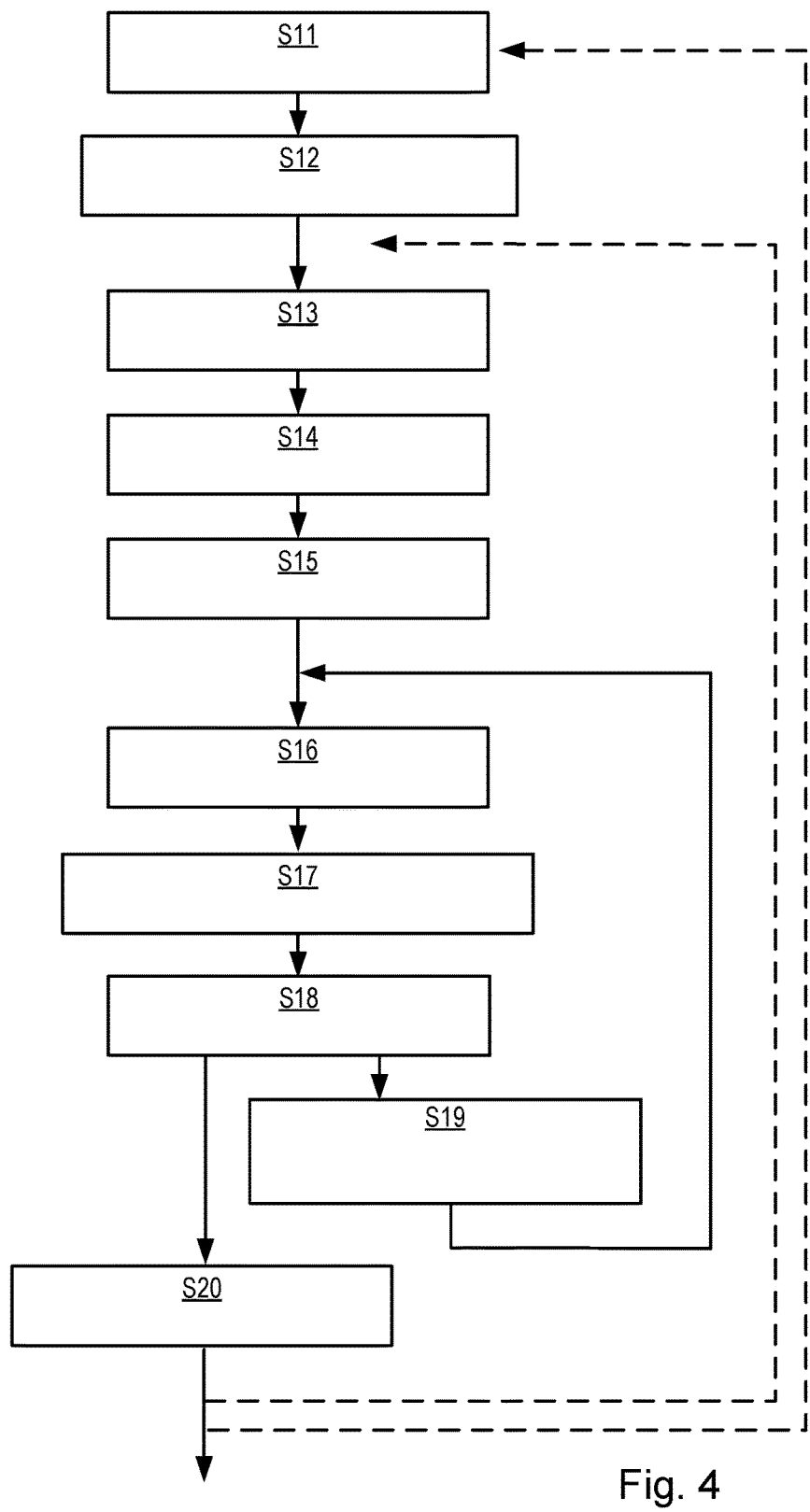
FIG. 4 is a flow chart illustrating a metrology method according to an embodiment of the present invention.
Figure 5:
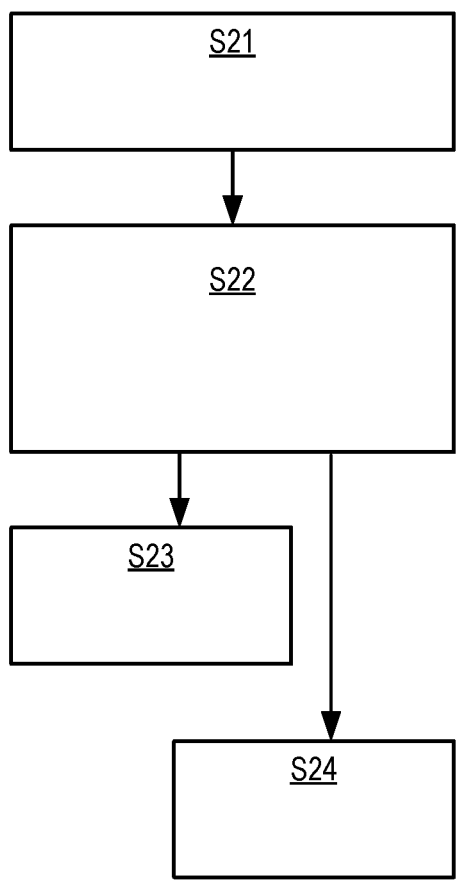
FIG. 5 is a flow chart illustrating a method of controlling performance of a metrology method and/or of a lithographic manufacturing process using measurements made by the method of FIG. 4.
Figure 6A:
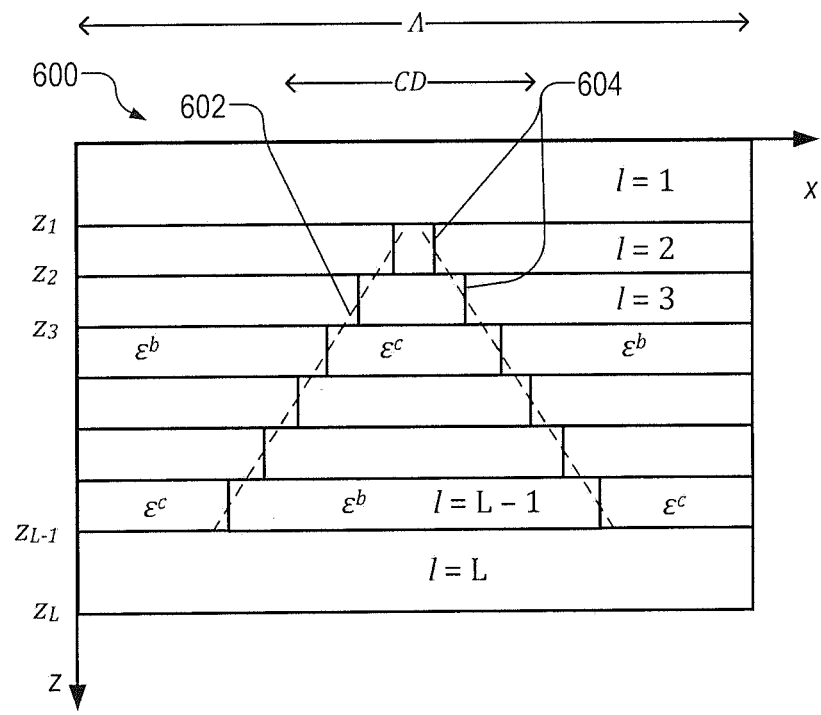
Figure 6B:
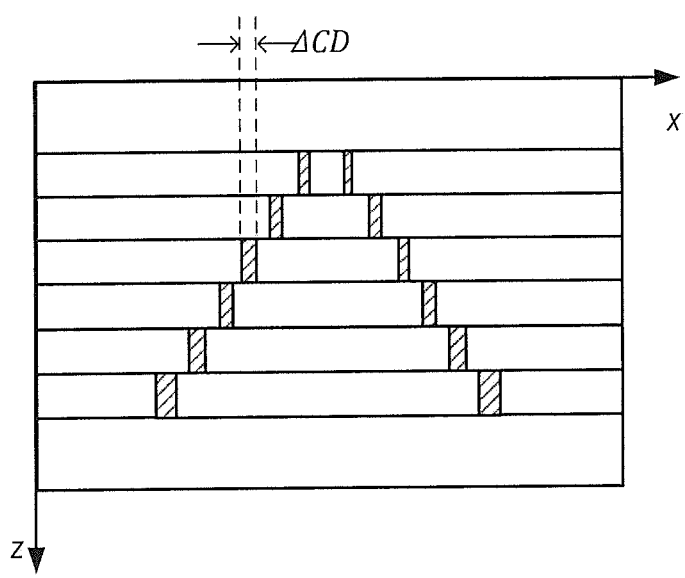
Figure 7:
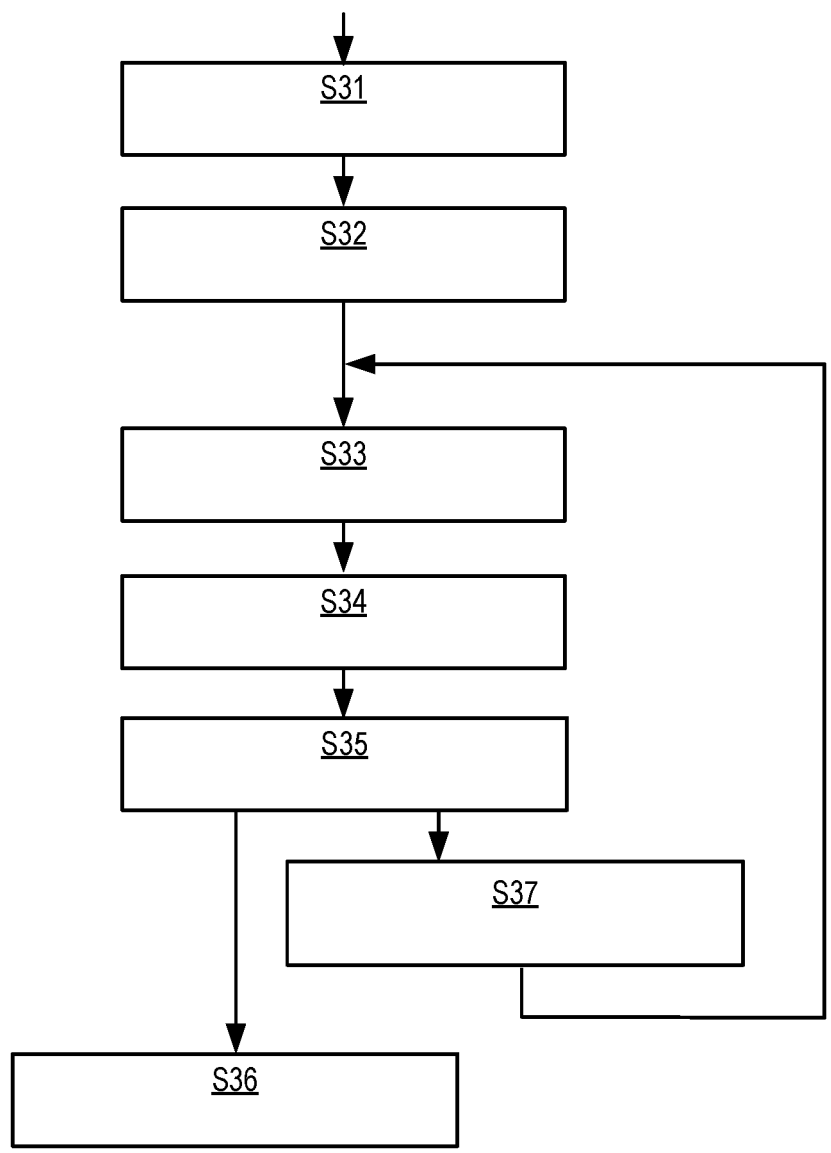
Figure 8:
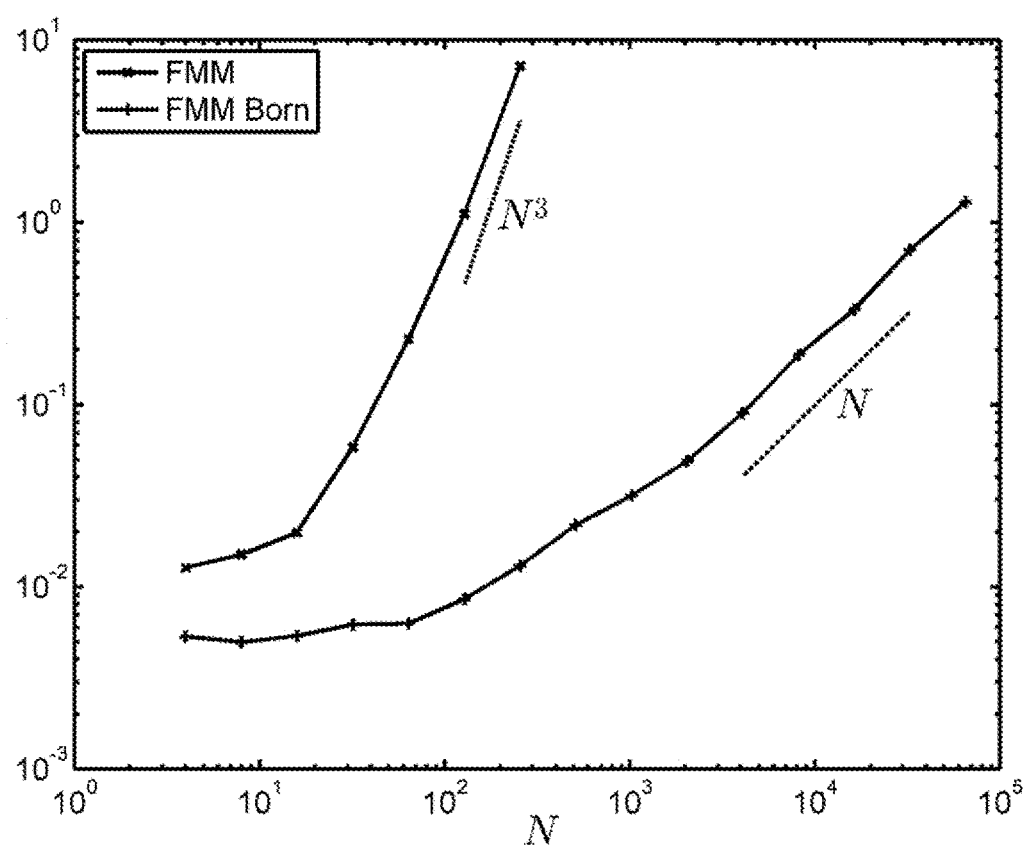
Figure 9:
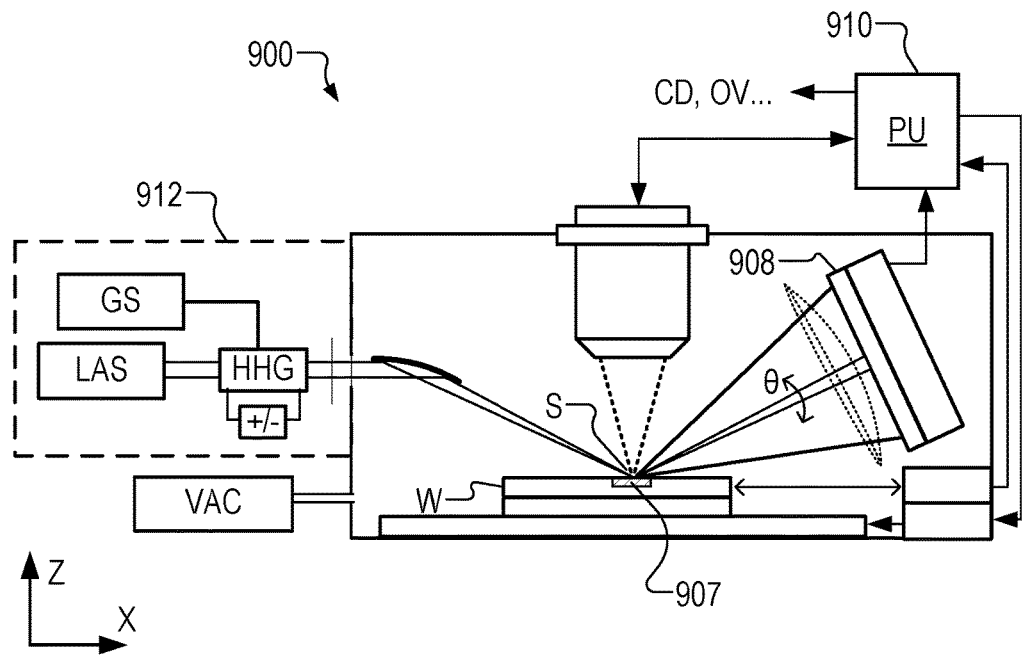
Figure 10:
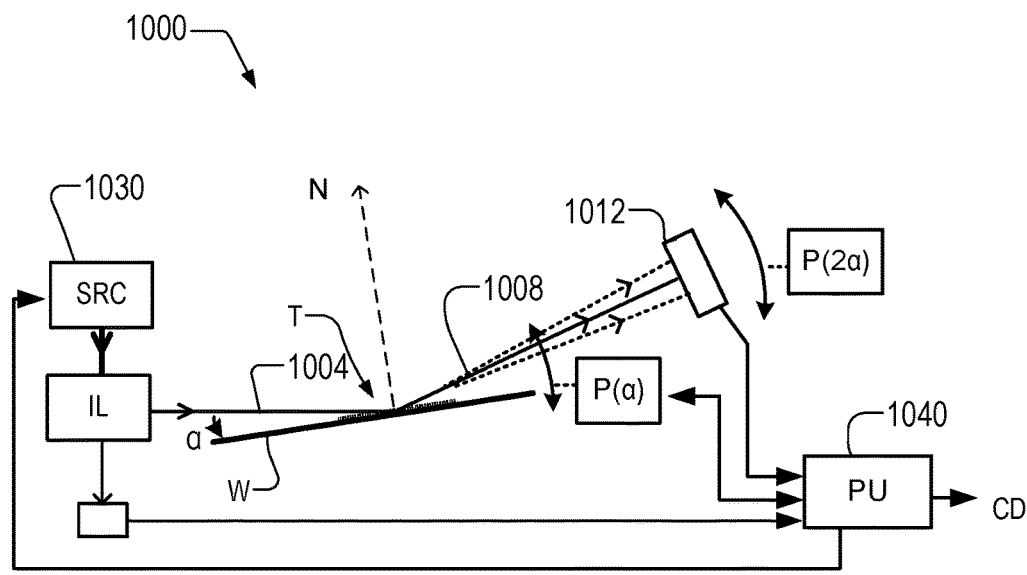

FIGS. 6(a) and 6(b) illustrates two forms of structure model that may be used in the method of FIGS. 4 and 5;

FIG. 7 illustrates in more detail steps of a modal method using the Born approximation, forming part of the method of FIG. 4 in one embodiment of the present invention;

FIG. 8 is a graph comparing computational complexity between a conventional Fourier modal method and a modified Fourier modal method according the present disclosure;

FIG. 9 illustrates schematically an apparatus for performing lensless imaging using EUV radiation reflected from a target structure; and FIG. 10 illustrates schematically a metrology apparatus based on reflection of x-ray and/or EUV radiation using an inverse Compton scattering source.

DETAILED DESCRIPTION OF EXEMPLARY EMBODIMENTS

Before describing embodiments of the invention in detail, it is instructive to present an example environment in which embodiments of the present invention may be implemented.

Lithographic Manufacturing Background

Figure 1:
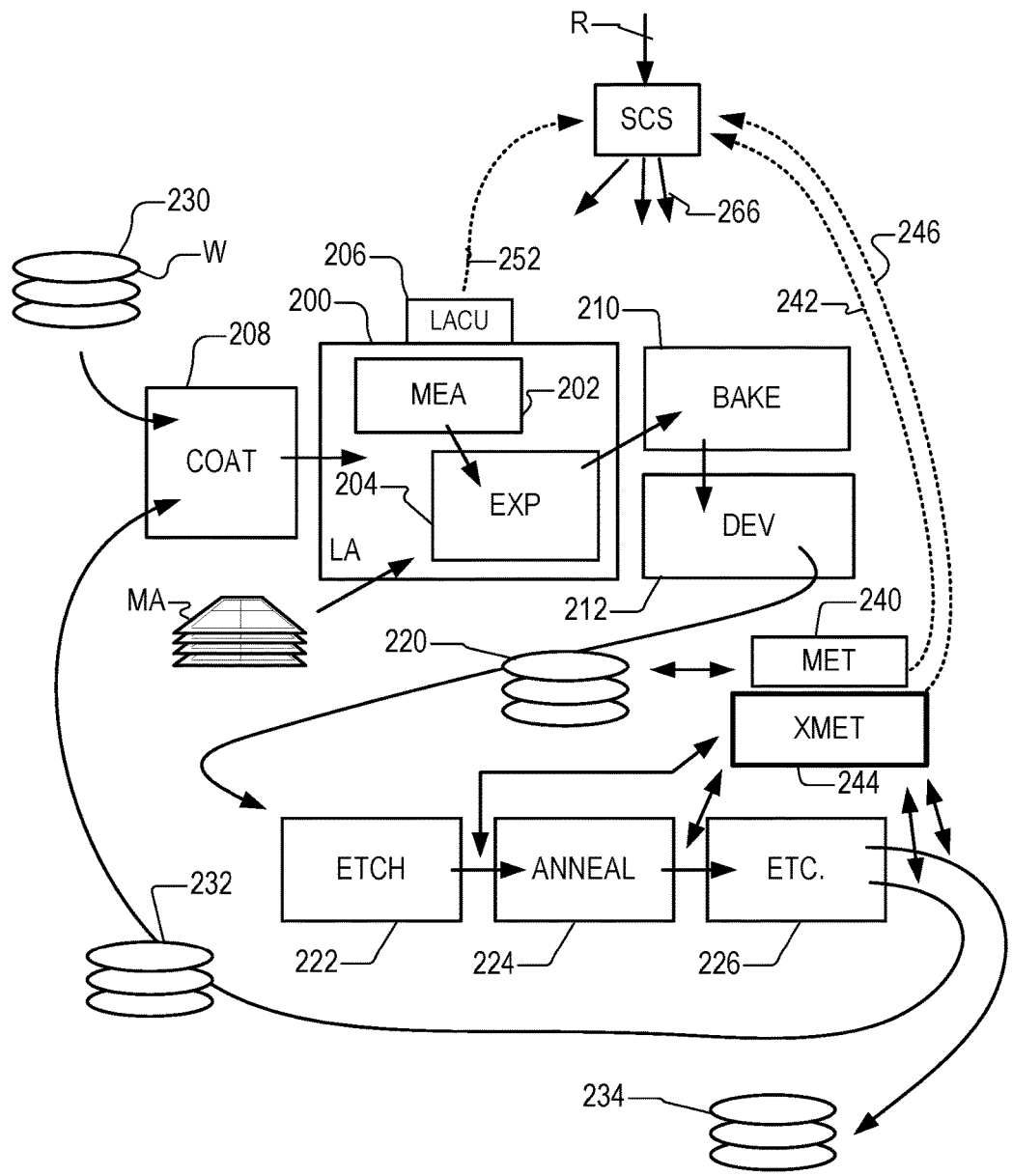
FIG. 1 depicts a lithographic apparatus together with other apparatuses forming a production facility for semiconductor devices.

FIG. 1 at 200 shows a lithographic apparatus LA as part of an industrial facility implementing a high-volume, lithographic manufacturing process. In the present example, the manufacturing process is adapted for the manufacture of for semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables WTa and WTb and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes metrology system which receives some or all of the substrates W that have been processed in the litho cell. Metrology results are provided directly or indirectly to the supervisory control system (SCS) 238. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Also shown in FIG. 1 is a metrology apparatus 240 which is provided for making measurements of parameters of the products at desired stages in the manufacturing process. A common example of a metrology apparatus in a modern lithographic production facility is a scatterometer, for example an angle-resolved scatterometer or a spectroscopic scatterometer, and it may be applied to measure properties of the developed substrates at 220 prior to etching in the apparatus 222. Using metrology apparatus 240, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work. Of course, metrology apparatus 240 and/or other metrology apparatuses (not shown) can be applied to measure properties of the processed substrates 232, 234, and incoming substrates 230.

Each generation of lithographic manufacturing technology (commonly referred to as a technology "node") has smaller feature sizes and tighter specifications for performance parameters such as CD. The transmissive small angle x-ray scatterometry (T-SAXS) has been investigated recently as a CD-metrology method solution for future technological nodes. T-SAXS offers benefits of high sensitivity, being robust against process variations and being selective for a parameter of interest. For this purpose, the manufacturing system illustrated in FIG. 1 includes one or more x-ray metrology apparatuses 244 in addition to the optical scatterometer 240. This x-ray metrology apparatus provides additional metrology results 246 which can be used by supervisory control system SCS to achieve further control of quality and improvement in performance of the lithographic manufacturing system as a whole. Whereas an optical scatterometer will often be used to inspect structures within the resist material treated within the litho cell, an x-ray metrology apparatus will more often be applied to measure structures after they have been formed in harder material. For example, substrates may be inspected using x-ray metrology apparatus 244 after they have been processed by the etching apparatus 222, annealing apparatus 224 and/or other apparatus 226.

X-Ray Metrology Introduction

Before describing the modified methods of simulating interaction of radiation with model structures that are the main aspects of the present, we shall briefly introduce the known technique of small angle x-ray scatterometry (T-SAXS). This T-SAXS technique is presented purely as one example of a practical application in which the disclosed method of simulation method can be used. The method of simulation can be applied in any x-ray diffraction application, including for example GI-SAXS (grazing incidence SAXS) and WAXS (wide-angle x-ray scatterometry), Other applications using EUV radiation, will be also illustrated further below.

Figure 2:
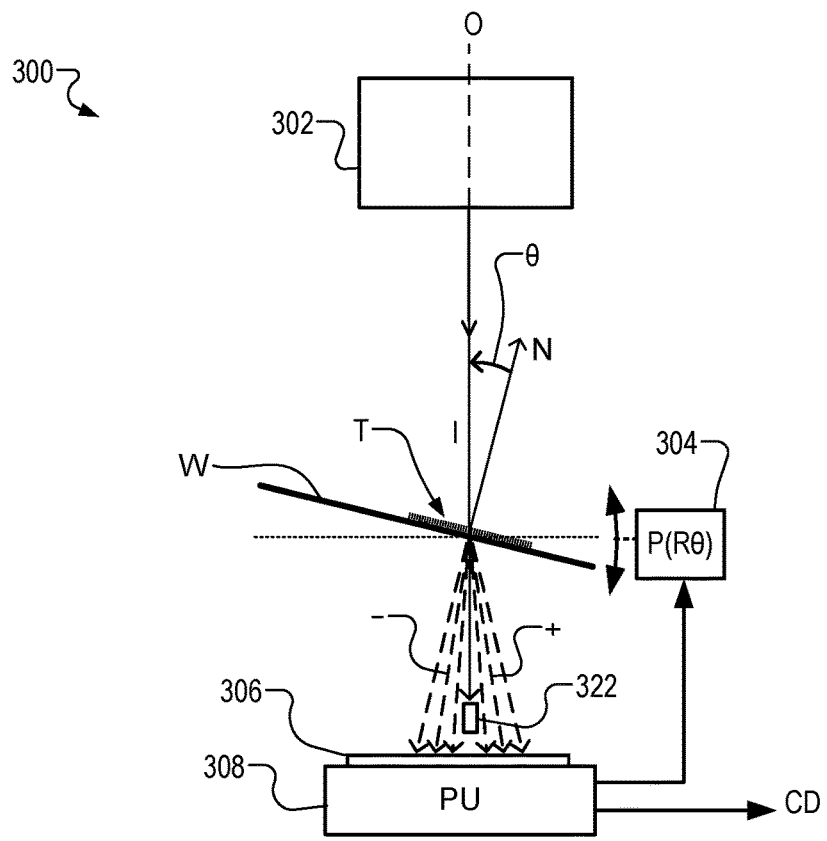
FIG. 2 depicts an x-ray metrology apparatus and optical metrology apparatus measuring a grating target on a substrate.

FIG. 2 illustrates an x-ray metrology apparatus 300 for use in measuring parameters of microscopic structures. These structures may be product structures or metrology targets formed on substrates processed in the manufacturing system of FIG. 1. The apparatus 300 may be used as the x-ray metrology apparatus 244 of FIG. 1. X-ray metrology apparatus 300 measures properties of a metrology target T formed on substrate W. An x-ray optical axis is represented simply by a dotted line O. A illumination system 302 provides a beam of X-ray radiation represented by ray I which forms a focused irradiation spot on target T. Substrate W is mounted on a movable support having a positioning system 304 such that an angle of incidence of ray I can be adjusted. In particular, known methods vary a polar angle θ, defined in this illustration as an angle between the direction of incidence of incident ray I and a direction N normal to the substrate. Other positioning systems may be provided to move the target into position at the irradiation spot. The radiation passes through target T and through substrate W and is scattered into a plurality of scattered rays before it impinges on detector 306. Detector 306 comprises for example a position-sensitive X-ray detector, typically an array of detector elements. The array may be a linear array, but by providing a 2-dimensional array of elements (pixels), diffraction patterns in both X and Y directions can be captured simultaneously. Detector 306 may be for example a CCD (charge coupled device) image sensor. A processor 308 receives signals from the detector and these are used in the processor to calculate a measurement of property of the target, for example CD or overlay.

Figure 3:
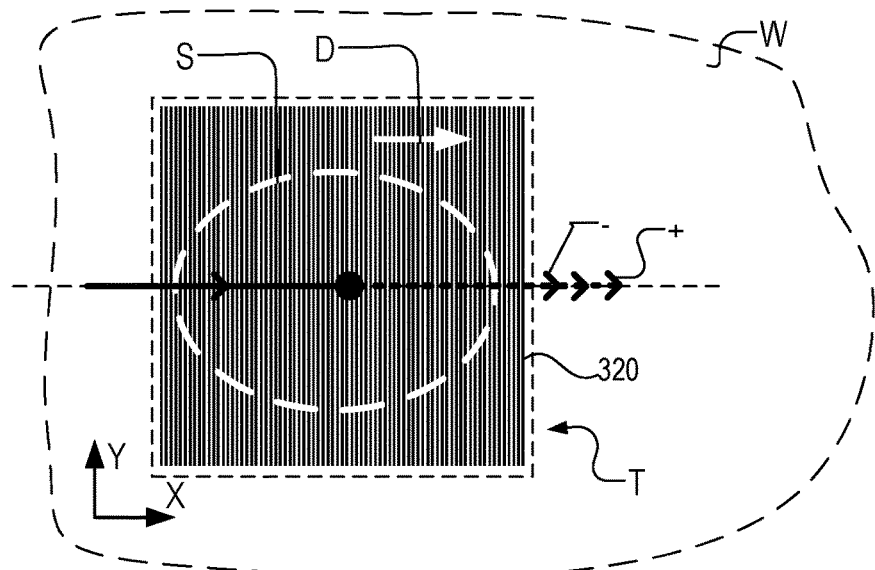
FIG. 3 shows in plan view the orientation of incident and scattered rays in the apparatus of FIG. 2 when measuring properties of a grating target.

Referring now to FIG. 3, we present a plan view of the substrate W with target T, viewed along the direction N normal to the substrate. We see that target T is a periodic structure having a direction of periodicity indicated by arrow D. In this example, where axes X and Y are defined in a coordinate system of the substrate W, the periodic structure comprises a number of lines 320 extending in the Y direction, so that the direction of periodicity D is aligned with the Y axis. The skilled person will appreciate that other targets may have grating lines arranged with a different orientation. In particular, a set of targets may be provided with both X and Y periodicity, two-dimensional gratings can also be provided, having two equal directions of periodicity, for example two directions orthogonal to one another. While a single representative beam is illustrated passing through the target, an oval S represents an example extent of the radiation spot. Incident rays will fall throughout the spot area. Conventionally the incident radiation is collimated within the illumination system 302 so that the incident rays are parallel to the extent possible. Spot S here is represented as an oval shape, on the assumption that the incident beam has a circular cross-section. The spot becomes elongated because of the non-zero angle of incidence θ.

In the illustrated example, a zero azimuthal angle of incidence is shown, meaning that the incident ray I and the direction of periodicity D lie together with the normal direction N in a common plane. Variations are also possible (not illustrated here) in which the angle of incidence of incident ray I can be varied not only in a polar angle θ, but also in an azimuthal angle φ. Examples of such variations are described in more detail in pending patent application PCT/EP2015/058238, mentioned above.

Referring back to FIGS. 2 and 3 together, it will be appreciated that some of the radiation transmitted through target T and substrate W is diffracted to different angles and detected at different positions on detector 306. As in an optical scatterometer, a periodic grating will in particular give rise to positive and negative diffraction orders, labeled schematically with '+' and '−' signs in the diagram. The positions and intensities of the different orders is recorded by detector 306 and may be referred to as a diffraction spectrum. The form of this diffraction spectrum (for example the relative intensities of diffraction orders within the diffraction spectrum) can be used to calculate the properties of the target structure. The angles are exaggerated in this schematic diagram, and very small angles may be seen in practice. The detector may be placed tens of centimeters or even meters from the substrate, in order for any spread of the orders to be resolved. However, the spread increases as the period of the structure shrinks, which makes x-ray metrology attractive for the future nodes. In practice, the intensity of the diffracted beams is also very weak in comparison with the incident the straight through (zero order) beam. A stop device 322 is generally provided to block the zero order beam so that the weaker signals are not overwhelmed at the detector.

The x-radiation may for example have a photon energy greater than 13 keV. It may have a wavelength less than 1 nm, or less than 0.1 nm in practice. The photon energy (hence wavelength) depends typically on the choice of anode material in a compact x-ray source. A wavelength of 0.073 nm is obtained for example from the k-alpha line of a Mo anode, while other anode materials such as SN are used.

Dimensions of the lines and spaces will depend on the target design, but the period of the structure may be for example less than 20 nm, even less than 10 nm and down to 5 nm. The lines 322 of the grating structure may be of the same dimension and pitch as product features in a product area of the substrate. The lines of the grating structure may in fact be the lines of a product structure, rather than a target structure formed within a dedicated target area, solely for the purposes of metrology. Such small features may be formed for example in an EUV lithography process, by imprint lithography or by direct-write methods. Such small features may also be formed using present-day DUV lithography, by a so-called double-patterning processes (generally multiple-patterning). Techniques in this category include pitch-doubling, for example by litho-etch-litho-etch (LELE) and self-aligned dual-damascene in back end-of the line (BEOL) layers. For the purposes of explanation, it will be assumed in the following examples that CD is the parameter of interest. However, where there are two gratings formed on top of one another, another parameter of interest maybe overlay. This can be measured based on asymmetry in the T-SAXS diffraction orders, as described separately in the pending patent application mentioned above. European patent application 14168067.8, filed on 13 May 2014 (not published at the present priority date) describes in detail the measurement of overlay using T-SAXS. The application further discloses a hybrid technique in which both optical scatterometry and x-ray metrology are used. The contents of the earlier application are hereby incorporated by reference.

In the application of T-SAXS to metrology on target gratings in semiconductor manufacturing, multiple diffraction spectra are captured using detector 306, while setting the polar angle of incidence θ to various different values. Optionally an azimuthal angle of incidence may be varied from zero, not illustrated in FIG. 2 but described in the pending patent application Ser. No. 14/168,067.8 mentioned above. The contents of that pending application are incorporated herein by reference. Using the detected spectra and a mathematical model of the target structure, reconstruction calculations can be performed to arrive at measurement of CD and/or other parameters of interest. An example reconstruction method will now be described below.

Introduction to Reconstruction

FIG. 4 is a flowchart of a method of measuring parameters of a target structure, using for example the above x-ray metrology apparatus and simulation methods disclosed herein. As described above, the target is on a substrate such as a semiconductor wafer. This target will often take the shape of a periodic series of lines in a grating, or structures in a 2-D array. The purpose of the metrology techniques is to measure one or more parameters of the shape by calculation from the observed interaction with radiation. In the reconstruction techniques disclosed herein, rigorous diffraction theories are used effectively to calculate what values of these parameters will result in a particular observed diffraction spectrum. In other words, target shape information is obtained for parameters such as CD (critical dimension) and overlay metrology. Overlay metrology is a measuring system in which the overlay of two targets is measured in order to determine whether two layers on a substrate are aligned or not. CD, or critical dimension, is the width of the object that is "written" on the substrate and is the limit at which a lithographic apparatus is physically able to write on a substrate. In some situations, the parameter of interest may be CD uniformity, rather than an absolute measurement of CD itself. Other parameters such as grating height and side wall angle may also be measured, if desired. Any parameter of the shape that has an influence on the diffraction pattern can in principle be measured in this way.

Using results from x-ray metrology apparatus 244 in combination with modeling of a target structure such as the target 30 and its diffraction properties, measurement of the shape and other parameters of the structure can be performed in a number of ways. In a first type of process, represented by FIG. 4, a diffraction pattern based on a first estimate of the target shape (a first candidate structure) is calculated and compared with the observed diffraction pattern. Parameters of the model are then varied systematically and the diffraction re-calculated in a series of iterations, to generate new candidate structures and so arrive at a best fit. In a second type of process, diffraction spectra for many different candidate structures are calculated in advance to create a 'library' of diffraction spectra. Then the diffraction pattern observed from the measurement target is compared with the library of calculated spectra to find a best fit. Both methods can be used together: a coarse fit can be obtained from a library, followed by an iterative process to find a best fit. It is expected that in T-SAXS the computation for the first type of process will not be burdensome. That being the case, there would be no need to resort to a library process. However, a library process may be appropriate in other applications and both types of reconstruction process are within the scope of the present disclosure.

Referring to FIG. 9 in more detail, the way the measurement of the target shape and/or material properties is carried out will be described in summary. The following steps are performed. The steps will be listed here, and then explained in more detail:

S11: Receive Substrate with Target(s)
S12: Define Measurement Recipe (φ, θ)
S13: Measure Diffraction Patterns
S14: Define Model Recipe
S15: Estimate Shape Parameters
S16: Calculate Model Diffraction Patterns
S17: Compare Measured v Calculated Patterns
S18: Calculate Merit Function
S19: Generate Revised Shape Parameters
S20: Report Final Shape Parameters At S11 a substrate W is received with one or more metrology targets T upon it. The target will be assumed for this description to be periodic in only one direction (1-D structure). In a case where it is periodic in two directions (2-dimensional structure), or not completely periodic, the processing will be adapted accordingly. At S12 a measurement recipe is defined, which in the enhanced method defines a range of one or more polar angles at which spectra are to be taken, and also defines a non-zero azimuthal angle. The optimum azimuthal angle for each type of target structure and manufacturing process can be determined by prior experiment and/or computational simulation. A recipe can be defined which measures a target using with two or more azimuthal angles, if desired. The recipe may also defined one or more combinations of wavelength and polarization for the incident radiation.

At S13 with a target structure positioned at the spot S, diffraction patterns of the actual target on the substrate are measured using T-SAXS in an apparatus as illustrated in FIG. 3. The measured diffraction patterns are captured by detector 406 and forwarded to a calculation system such as processor 408. To obtain a robust measurement through reconstruction, several spectra of the same target may be captured with different angles θ and φ.

Note that the diffraction patterns may be processed as detailed spectra, or they may be simplified into a set of parameters before being used in calculations. As a particular example, the diffraction pattern may be reduced simply to a set of values representing the intensity of identifiable diffraction orders. The intensity may be obtained for example by identifying a peak in the diffraction spectrum that corresponds to a respective diffraction order, and assigned to that diffraction order a value corresponding to the height of the observed peak.

At S14 a 'model recipe' is established which defines a parameterized model of the target structure in terms of a number of parameters $p_i$ ($p_1$, $p_2$, $p_3$ and so on). These parameters may represent for example, in a 1-D periodic structure, the angle of a side wall, the height or depth of a feature, the width of the feature. Properties of the target material and underlying layers are also represented by parameters such as refractive index (at a particular wavelength present in the x-radiation beam). Importantly, while a target structure may be defined by dozens of parameters describing its shape and material properties, the model recipe will define many of these to have fixed values, while others are to be variable or 'floating' parameters for the purpose of the following process steps. For the purposes of describing FIG. 4, only the variable parameters are considered as parameters $p_i$.

At S15 a model target shape is estimated by setting initial values NO) for the floating parameters (i.e. $p_1(0)$, $p_2(0)$, $p_3(0)$ and so on). Each floating parameter will be generated within certain predetermined ranges, as defined in the recipe.

At S16, the parameters representing the estimated shape, together with the properties of the different materials in the model, are used to calculate the scattering properties, for example using a rigorous optical diffraction method such as the modified FMM or other solver of Maxwell equations, described in more detail below. This gives an estimated or model diffraction pattern of the estimated target shape, for a given combination of wavelength, angles θ and φ and so forth.

At S17 and S18 the measured diffraction patterns and the model diffraction patterns are then compared and their similarities and differences are used to calculate a "merit function" for the model target shape.

Assuming that the merit function indicates that the model needs to be improved before it represents accurately the actual target shape, control passes to step S19 where new parameters $p_1(1)$, $p_2(1)$, $p_3(1)$, etc. are estimated and fed back iteratively into step S16. Steps S16 to S18 are repeated. In order to assist the search, the calculations in step S16 further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

When the merit function indicates that this iterative process has converged on a solution with a desired accuracy, control passes to step S20 and the currently estimated parameters (for example a CD value) are reported as the measurement of the actual target structure.

Once the value for one target has been calculated, a new target on the same substrate or a similar substrate may be measured using the same steps S13 etc., without changing the measurement recipe. Where a different type of substrate or target is to measured, or in any case where it is desired to change the measurement recipe, control passes to step S11 or S12 instead.

FIG. 5 illustrates the application of a measurement method (for example the method of FIG. 4) in the management of a lithographic manufacturing system. The steps will be listed here, and then explained in more detail:

S21: Process wafer to produce structures on substrate
S22: Measure CD and/or other parameter across substrate
S23: Update metrology recipe
S24: Update lithography and/or process recipe At step S21, structures are produced across a substrate using the lithographic manufacturing system. At S22, the x-ray metrology apparatus and optionally other metrology apparatus and information sources are used to measure a property of the structures across the substrate. At step S23, optionally, metrology recipes and calibrations of the x-ray metrology apparatus and/or other metrology apparatus 240 are updated in light of the measurement results obtained. For example, where the x-ray metrology apparatus 244 has a lower throughput than the optical metrology apparatus 240, a few accurate measurements using x-rays can be used to improve the calculation of measurements made using the optical metrology apparatus, for a specific substrate design and process.

At step S24, measurements of CD or other parameters are compared with desired values, and used to update settings of the lithographic apparatus and/or other apparatus within the lithographic manufacturing system. By providing an x-ray metrology apparatus. Product features and/or product-like features can be measured directly, even at the smallest technology nodes, and in-die targets can be provided and measured without losing too much area.

Solving Maxwell's Equations with Born Approximation

In the methods illustrated in FIG. 4, the computation time of this iterative process is largely determined by the forward diffraction model used to simulate interaction of radiation with a target structure (i.e. step S16). As mentioned in the introduction, when radiation wavelengths are short in relation to the domain size, then there are more degrees of freedom and the calculation time increases very rapidly as the number of degrees of freedom increases in each dimension. (Additionally the number of floating parameters represents further degrees of freedom in the overall iterative reconstruction process, but that is independent of the degrees of freedom in each simulation step S16.) As noted in the introduction above, the Born approximation ought to be attractive to use in this type of reconstruction. In order to find the numerical solution of the integral formulation of the Born approximation, a full discretization (in all spatial dimensions) is required. The product sx*sy*sz mentioned above can easily reach a factor of 1000, and the computation might become expensive. Moreover, due to discretization in the z direction, the solution is prone to approximation errors in all directions. Roughly speaking, the computational burden of such a method scales as N^3(N cubed), due to the requirement for operations such as eigenvalue computation and matrix inversion. N may be for example several hundred, leading to excessive computational burden.

In the present disclosure, we propose a new formulation of a modal method which is specifically tailored for a fast semi-analytical solution of the Maxwell's equations in Born approximation. As will be seen, a standard homogeneous differential equation for the total field is converted into a non-homogeneous differential equation for the scattered field containing the total field on the right-hand side. The solution procedure for the non-homogeneous equation is the same as the approach described in References (5) and (6), with appropriate modifications.

The inventors have recognized that applying the Born approximation in a modal method diagonalizes the discrete matrix equation. Thus, all the O(1N^3) (order N^3) operations, such as the eigenvalue computation and matrix inversion, are avoided. This results in a numerical method that has two important advantages with respect to the approaches discussed above. Firstly, it features a reduced complexity of order N, as opposed to the order N^3 complexity of the FMM without Born. Secondly, the number of degrees of freedom is independent of sz as opposed to the integral method with Born. Although there is still a division into layers in the z direction, the number of slices is independent of the wavelength. In this situation, N is proportional to sx*sy. In a one-dimensional solution, either sx or sy is reduced to 1. As in the traditional FMM, the z-dependent part of the solution can be derived analytically.

FIG. 6(a) illustrates the form of a parameterized structure model 600 suitable for use in a method according to the present disclosure. This particular example represents a one-dimensional grating, comprising notionally an infinite number of repetitions of a repeating unit with length Λ. The direction of periodicity in this example is the x direction, represented by a horizontal axis. The structure is modeled as a series of layers or slices, with slice index l ranging from 1 to L. The extent of each slice in the z directions is given by $z_0 < z_1 < \ldots < z_{L-1} < z_L$, as illustrated. The structure as a whole, and within each layer is considered to be homogeneous in the y direction. In top and bottom layers 1 and L, the material of the modeled structure is homogeneous in the x direction. In the intervening layers, a line or bar feature with sloping profile 602 is represented by a contrast feature 604, so that the sloping sides of the modeled structure are represented in a staircase approximation by the vertical sides of the contrast features in the series of layers. For each of these layers, a background permittivity $\varepsilon^b$ is present for some x values, and a feature permittivity c is present at others. Again, the background permittivity may vary between layers, though it does not vary within a layer. With a view to applying the Born approximation, the background permittivity $\varepsilon^b$ for a given layer can be selected to match whichever of the two materials is predominant in that layer. Thus, in the lowest layer L−1 of the structure shown in FIG. 6, the roles of the line feature and the surrounding material are reversed and the material of the line feature is considered as the background $\varepsilon^b$.

In the implementation of the Fourier modal method to be described below, the permittivity in the non-homogeneous layers is modeled by two separate components: a background permittivity $\varepsilon^b$ which is independent of x, and a contrast permittivity $\varepsilon(x, z)$ which is zero for most x values and has a non-zero value only where x falls within the contrast feature 604. This non-zero value represents the difference between the feature permittivity $\varepsilon^c$. In alternative embodiments, the background permittivity can be allowed to vary in a layer, to model a particular structure. This is not excluded in the methods of the present disclosure, but it may not yield the computational advantages that are available when the background permittivity is constant per layer.

Also labeled in FIG. 6(*a*) is critical dimension or linewidth CD, which is an example of a parameter of the shape of the modeled structure that may be the parameter of interest in a metrology application. Other parameters of the shape will include the height of the line feature, the sidewall angles of the sloping profile 602, and possibly material properties such as permittivity. The bottom layer L may represent substrate material, and multiple bottom layers may be provided, according to the structure being modeled. Similarly, the background material represented by background permittivity in a given layer may be air or a vacuum, or some solid material surrounding the contrast feature 604.

The structure model does not have to represent directly the real structure. In another application, the structure model represents difference between structures. FIG. 6(*b*) illustrates a structure model 610 of this type. The real structure corresponding to this model 610 is the same as in FIG. 6(*a*), but the model structure represents only differences between structures with different values of (for example) CD. Therefore in this model all regions are regarded as background except the shaded regions with width ΔCD. The contrast permittivity thus represents only the difference between a structure having one value of parameter CD and a perturbed structure having another value of CD. Using such a differential model the application changes from computing the interaction of radiation with a structure to computing sensitivities of this interaction to changes in geometry. Nothing changes in the numerical methods, and it should be understood that differential models such as this are within the scope of the term "structure model" as used in the introduction and claims.

Now, FIG. 7 is a flowchart summarizing the FMM or other modal method process as applied in the reconstruction method of FIG. 4, step S16. The method of FIG. 7 is generally one of simulating interaction of radiation with a structure based on a parameterized model. The method of FIG. 7 can be applied in other fields than the specific application of FIG. 4 and semiconductor metrology by scatterometry in x-ray and/or EUV ranges. For example, the method can be applied to other material analysis fields such as crystallography and bio-crystallography. Other fields of application may include for example coherent diffraction imaging (CDI, lensless imaging), which can also benefit from the fast forward diffraction calculations. Steps of the method will be listed here and then explained in more detail.

S31: Express Maxwell equations in Born approximation
S32: Express model in modal form
S33: Solve layers analytically
S34: Connect and solve structure
S35: Higher order wanted?
S36: Report solution
S37: Substitute new total field and repeat In step S31, the Maxwell equations for the structure model and the incident radiation in the Born approximation are expressed as differential equations to be solved per layer. In step S32, the parameterized model of the target structure is received and, if necessary, convert to express it in modal form. In the Fourier modal method, the contrast function within each layer will be expressed in terms of spatial frequency components, up to the specified number N of single-sided harmonics. In step S33, the analytical solution for each layer is calculated. In step S34, the solutions for the layers are connected by enforcing continuity conditions, and the system of equations is solved for the structure model as a whole.

At step S36, it is determined whether a higher order Born approximation is wanted. Second and higher order Born approximations are performed by repeating the approximate solution of Maxwell's equations, using each time the calculated total field as the background field as an approximation for the true total field. If no higher Born approximation is wanted, the solution obtained in step S34 is reported as the simulated scattered radiation from the structure. If a higher order approximation is desired, in step S37 the approximate total field just calculated is applied as a substitute approximation for the true total field, and the procedure returns to step S33 for another iteration.

A mathematical description and justification of the method of FIG. 7 method according to the present disclosure using the simple model of FIG. 6 will now be presented. The particular modal method used in the following examples will be Fourier modal method (FMM) or RCWA (rigorous coupled-wave analysis). Modes in FMM are conveniently referred to as harmonics. In the example of a periodic structure, these harmonics are spatial frequency components having frequencies based on integer multiples of the fundamental periodic frequency of the structure.

The time-harmonic Maxwell equations satisfied by the total electric and magnetic fields $e^t$ and $h^t$ are given by $$\nabla \times e^t(x) = -k_0 h^t(x), \quad (1a)$$

$$\nabla \times h^t(x) = -k_0 \varepsilon(x,z) e^t(x). \quad (1b)$$

Here, x=(x, y, z) is the vector of coordinates, $\varepsilon(x, z)$ is the electric permittivity chosen as y-independent, and $k_0$ is the vacuum wavenumber. The latter is related to the vacuum wavelength λ via $$k_0 = \frac{2\pi}{\lambda}. \quad (2)$$

As explained with reference to FIG. 6 that the geometry, described by ε, has been chosen to be periodic in x and invariant in y. Similarly, the time-harmonic Maxwell equations satisfied by the background fields $e^b$ and $h^b$ for a given background permittivity $\varepsilon^b$ read $$\nabla \times e^b(x) = -k_0 h^b(x), \quad (3a)$$

$$\nabla \times h^b(x) = -k_0 \varepsilon^b(z) e^b(x). \quad (3b)$$

The background geometry is chosen to be independent of x and is represented by a stack of homogeneous layers. The background material $\varepsilon^b(z)$ is chosen equal to the material that is predominant in the non-homogenous layers and $\varepsilon^b = \varepsilon$ in the homogeneous layers. As explained above, the implementation is free to choose freely which of two or more materials in the modeled structure is regarded as the "background" material in each layer.

Subtracting Equation (3) from Equation (1) and introducing the contrast electric and magnetic fields $$e(x) = e^t(x) - e^b(x), \quad (4a)$$

$$h(x) = h^t(x) - h^b(x), \quad (4b)$$

yields the contrast-field formulation $$\nabla \times e(x) = -k_0 h(x), \quad (5a)$$

$$\nabla \times h(x) = -k_0 \varepsilon(x,z) e(x) - k_0 (\varepsilon(x,z) - \varepsilon^b(z)) e^b(x). \quad (5b)$$

It is this formulation that is solved by the aperiodic Fourier modal method in contrast-field formulation (AFMM-CFF) in Reference (7). To apply the Born approximation we rewrite Equation (5) as $$\nabla \times e(x) = -k_0 h(x), \quad (6a)$$

$$\nabla \times h(x) = -k_0 \varepsilon^b(z) e(x) - k_0 (\varepsilon(x,z) - \varepsilon^b(z)) e^t(x). \quad (6b)$$

If the contrast $\varepsilon(x,z) - \varepsilon^b(x,z)$ is small, the Born approximation $$(\varepsilon(x,z) - \varepsilon^b(z)) e^t(x) \approx (\varepsilon(x,z) - \varepsilon^b(Z)) e^b(x) \quad (7)$$

applied to Equation (6) yields $$\nabla \times e(x) = -k_0 h(x), \quad (8a)$$

$$\nabla \times h(x) = -k_0 \varepsilon^b(z) e(x) - k_0 (\varepsilon(x,z) - \varepsilon^b(z)) e^b(x). \quad (8b)$$

Comparing Equation (8) to (6) we observe that the only difference is in the second term on the right-hand side of the second equation, where the total field has been replaced by the background field. It can be shown in the next sections that this approximation significantly speeds-up the calculations compared with what would be expected. To discretize and solve the problem an approach similar to the aperiodic FMM in contrast-field formulation described in Reference (7) will be used. However, the particular solution used has a different form than the one derived in Reference (7).

The differential equations in Equation (2) are complemented by periodic boundary conditions on the lateral sides, radiation boundary conditions in the upper and lower half-spaces, as well as an incident field $$e^{inc} = t_{inc}^e e^{-ik^{inc} \cdot x}. \quad (9)$$

Here, $t_{inc}^e$ contains the complex-valued amplitudes of the three spatial components of the incident field and $k^{inc}$ is a wave vector.

In order to show the results of the method on simpler cases we will present here the mathematical formulation for planar incidence with TE polarization. The formulation for TM polarization can be found likewise, and a complete formulation for conical diffraction follows similar lines. The observations below about computational complexity hold for these general cases also.

To discretize the problem in a manner similar to the standard FMM, we divide the domain into L slices (see FIG. 6). The above contrast field equations (8) in the Born approximation can be expanded in terms of partial derivatives in x, y, z for each slice. The full derivation is very detailed, however, and omitted here for conciseness. Summarizing it, after expanding in the x direction we apply a Galerkin approach with "shifted" (or pseudo-periodic) Fourier harmonics $\phi_n$ as basis functions and test functions. In each slice l, the contrast fields (electric and magnetic) are expanded in each of the three directions.

To present the differential equation that is to be solved for the special case of TE polarized incident radiation, we first define vectors $s_{\alpha,l}^b(z)$, $u_{\alpha,l}^b(z)$ of the form $$s_{\alpha,l}^b(z) = d_0 s_{\alpha,l}^b(z) = d_0 (t_{\alpha,l}^e e^{-k_0 q_l (z - z_{l-1})} + r_{\alpha,l}^e e^{k_0 q_l (z - z_l)}), \quad (10a)$$

$$u_{\alpha,l}^b(z) = d_0 u_{\alpha,l}^b(z) = d_0 (t_{\alpha,l}^h e^{-k_0 q_l (z - z_{l-1})} + r_{\alpha,l}^h e^{k_0 q_l (z - z_l)}), \quad (10b)$$

Here $d_0 \in R^{2N+1}$ is an all-zero vector except for entry N+1. This special form of the vector $d_0$ is due to the fact that the background field only consists of a zeroth order. For a second- or higher-order Born approximation (discussed further below) this will not be the case. The value of $q_l$ is given by $$q_l = \sqrt{\left(\frac{k_x^{inc}}{k_0}\right)^2 - \left(\frac{k_y^{inc}}{k_0}\right)^2 - \varepsilon_l^b}. \quad (11)$$

Here branch cut is chosen such the square root of a negative real number is in the upper half-space in the complex plane.

The coefficients $t_{\alpha,l}^e$, $r_{\alpha,l}^e$, and $t_{\alpha,l}^h$, $r_{\alpha,l}^h$ in Equation (10) are the amplitudes of the downward and upward traveling waves corresponding to the electric and magnetic background field. They can be determined by solving the Fresnel reflection-transmission problem for a multilayer with a known incident field in the superstrate $t_1^e = t_{inc}^e$, $t_1^h = t_{inc}^h$ and no incident field in the substrate $t_L^e = t_L^h = 0$. A suitable method for this step is presented in Chapter 5 of the textbook, P. Yeh, Optical Waves in Layered Media (Wiley Series in Pure and Applied Optics) (Wiley-Interscience, 2005), 2nd ed. Next we apply the Galerkin method with a standard inner product on the interval $x \in [0, \Lambda)$ to the expanded contrast field equations mentioned above.

In the full derivation, the equations have not been simplified, such that they apply to the general case of conical diffraction. In order to show the essence of the method on simpler cases we will present the mathematical formulation for a simple case of planar incidence with TE. The formulation for TM polarization and one for complete formulation for conical diffraction follow similar lines. In the case of planar incidence and TE polarization we have $s_x = s_z = u_y = 0$ and $s_x^b = s_z^b = u_y^b = 0$. Substituting these expressions into the discretized Maxwell equations for the contrast field mentioned above, we obtain a system of differential equations expressed in matrix form as $$\frac{d^2}{dz^2} s_{y,l}(z) = k_0^2 Q_l^2 s_{y,l}(z) - k_0^2 B_l s_{y,l}^b(z), \quad (12)$$

Here $Q_l$ and $B_l$ are matrices known to those familiar with modal methods. They can be defined by expressions $Q_l=(K_x^2-E_l^b)^{1/2}$ and $B_l=E_l-E_l^b$. Matrix $Q_l$ is referred to in the art as the "system matrix", because it defines the system of differential equations to be solved. Matrices used in these definitions are in turn defined as follows, $$(K_x)_{mn}=(k_{xn}/k_0)\delta_{mn}, \quad (13)$$

$$(K_y)_{mn}=(k_y/k_0)\delta_{mn}, \quad (14)$$

$$(E_l)_{mn}=\hat{\varepsilon}_{l,n-m}, \quad (15)$$

$$(E_l^b)_{mn}=\hat{\varepsilon}_{l,n-m}^b, \quad (16)$$

Here $\delta_{mn}$ is the Kronecker delta which has value 1 when m and n are equal, and zero otherwise. Consequently, it is known that system matrix $Q_l$ is a diagonal matrix.

For simplicity we drop the component subscript y and the layer index l and write the system of ordinary differential equations in a component-wise form, $$\frac{d^2}{dz^2}s_n(z) = k_0^2 q_n^2 s_n(z) - k_0^2 b_{n0}(te^{-k_0q_0z} + re^{k_0q_0z}), \quad (17)$$

Here $b_{nm}$ is the (n, m) element of the matrix $B_l$ and $q_n$ is the n-th element on the diagonal of $Q_l$.

Now the full general solution of Equation (17) can be derived by methods shown in Reference (7) and written as $$s_{y,l}(z) = s_{y,l}^{hom}(z) + s_{y,l}^{part}(z) = \quad (18)$$
$$e^{-k_0Qz}c^+ + e^{k_0Qz}c^- + (I-D+zD)(e^{-k_0q_0z}p^+ + e^{k_0q_0z}p^-),$$

Here $(D)_{mn}=\delta_m\delta_n$ for m, n=−N, . . . , +N. Again $\delta_{mn}$ is the Kronecker delta, with the result that D i.e. a matrix whose elements are all zero, except the entry in the center equal to one.

Having obtained general solutions for the Maxwell equations in Born approximation in each layer, it remains to connect the individual solutions into a solution for the whole of the modeled structure 600. At the interface between layers, continuity of the tangential components of the fields is required. This condition holds for the contrast field as a result of the continuity of tangential components of the total and background fields. Substituting a result from earlier in the derivation yields $$s_{y,l}(z_l) = s_{y,l+1}(z_l), \quad (19a)$$

$$k_0^{-1}\frac{d}{dz}s_{y,l}(z_l) = k_0^{-1}\frac{d}{dz}s_{y,l+1}(z_l). \quad (19b)$$

We define $$X_l = e^{-k_0Q_l(z-z_{l-1})}, \quad (20a)$$

$$V_l = -Q_l. \quad (20b)$$

Then, from equations (19) and (18) we have for each slice $$\begin{bmatrix} X_l & I \\ V_lX_l & -V_l \end{bmatrix}\begin{bmatrix} c_l^+ \\ c_l^- \end{bmatrix} + g_l(z_i) = \quad (21)$$
$$\begin{bmatrix} I & X_{l+1} \\ V_{l+1} & -V_{l+1}X_{l+1} \end{bmatrix}\begin{bmatrix} c_{l+1}^+ \\ c_{l+1}^- \end{bmatrix} + g_{l+1}(z_i),$$

where $$g_l(z) = \begin{bmatrix} \bar{g} \\ k_0^{-1}\frac{d}{dz}\bar{g} \end{bmatrix}, \quad (22)$$

and $$\bar{g} = (I-D+zD)(e^{-k_0q_0z}p^+ + e^{k_0q_0z}p^-), \quad (23a)$$

$$\frac{d}{dz}\bar{g} = (I-D+zD)(-k_0q_0e^{-k_0q_0z}p^+ + k_0q_0e^{k_0q_0z}p^-) + D(e^{-k_0q_0z}p^+ + e^{k_0q_0z}p^-). \quad (23b)$$

The radiation condition is imposed by requiring that coefficients of the incoming waves in layers 1 and L vanish, $$c_1^+ = 0, \, c_L^- = 0. \quad (24)$$

We consider now the computational burden involved in performing the method of FIG. 7 based on the particular form of Born approximation and Fourier modal method described above. In the Fourier modal method for the rigorous Maxwell's equations (i.e. without the Born approximation) there are two expensive O(N^3) operations: the eigenvalue decomposition and the solution of the recursive system via a non-homogeneous S-matrix approach described in Reference (8). We explain now that the complexity of these steps is reduced to O(N) when using the first Born approximation in a Fourier modal method in the manner described above.

As already mentioned, the application of the Born approximation expressed in the form used above diagonalizes the system matrix $Q_l$ in the second-order differential Equation (12). In this way the first expensive operation of the method, the eigenvalue decomposition, is avoided. The computation of the diagonal matrix $Q_l$ is an O(N) operation.

The non-homogeneous S-matrix approach solves the recursive linear systems represented in Equation (21). Here, all matrices are diagonal except the matrix $E_l$ in the non-homogeneous term $g_l(z)$. We observe that the matrix $E_l$ appears always in a product with a vector (and not with another matrix). For an arbitrary matrix, its product with an arbitrary vector is an O(N^2) operation. However, when the background field consists of only zeroth-order plane waves, the vector in the matrix-vector product has a single non-zero element and the matrix-vector product reduces to selecting the corresponding column in the matrix and multiplying it with the non-zero entry of the vector. This results in an (overall) O(N) complexity. In other words, where the value of N may be several hundred, the reduction in computational complexity achieved in the disclosed method can be several orders of magnitude.

For a second- or higher-order Born approximation, all orders of the background field are non-zero and the matrix vector product with $E_l$ cannot be computed in linear time. However, the matrix $E_l$ is a Toeplitz matrix which implies that an efficient matrix-vector product is possible by embedding the Toeplitz matrix into a circulant matrix and using FFTs (Fast Fourier Transform) to compute the product of the latter with a zero-padded vector. This results in a O(N log N) complexity. Again, while a linear complexity has not been achieved, the complexity may still be several orders of magnitude lower than the O(N^3) complexity involved in the conventional FMM.

The techniques disclosed herein may be applied in other types of modal methods, besides FMM. These other modal methods may be based for example on piecewise linear functions, piecewise-constant functions, higher-degree polynomials, Bloch modes, Legendre polynomials, splines such as B-splines, and wavelets. The computational saving may vary depending on the basis. The matrix Q will be diagonal independent of the basis. The matrix $E_l$ that is Toeplitz for Fourier modes may have a different structure. Typically, widely used basis functions induce a structure that allows us to have a complexity of N or N log N. For instance, for local polynomial basis functions, matrix $E_l$ becomes sparse and the complexity is linear.

Of course, besides a reduction in the computational complexity, it is important to understand in what cases and to what extent the Born approximation will deliver a sufficiently accurate simulation of the interaction of radiation with the real structure. In this section we study the complexity of the FMM in Born approximation and the validity of the approximation for some cases of interest. A study has been made with a simplified one-dimensional periodic stack, similar to the one shown in FIG. 6 but with only a single non-homogeneous layer.

Referring again to FIGS. 2 to 5, an important application that makes use of the Born approximation in other Maxwell solvers is the reconstruction of critical dimension parameters using small-angle X-ray scattering (CD-SAXS) in lithography. We have studied the validity of the Born approximation for the simplified stack with planar illumination and a wavelength $\lambda=0.073$ nm. The angle $\theta$ is defined as the angle between the wavevector $k^{inc}$ and the (positive) z-axis. In the simulations we have chosen $\theta=\pi/12$ which corresponds with the schematic arrangement illustrated in FIG. 2. The refractive index of the contrasting feature 604 is defined as $$n=\sqrt{\varepsilon}=1-\delta-i\beta. \qquad (86)$$

To assess the quality of the Born approximation we define absolute and relative errors respectively by $$E_{abs} = RR^* - R_{ref}R_{ref}^*, \qquad (87)$$

$$E_{rel} = \frac{RR^* - R_{ref}R_{ref}^*}{R_{ref}R_{ref}^*}. \qquad (88)$$

Here R denotes the complex first-order reflection coefficient. The reference $R_{ref}$ is obtained with a full rigorous FMM with 1001 harmonics (N=500). Simulations were performed for X-ray illumination, $\lambda=0.073$ nm (Mo $K_\alpha$) in both TE and TM polarizations.

As expected, it was found that the error introduced by the Born approximation increases as the contrast with respect to the background material increases. The behavior of the errors is however closer to a max($\delta$, $\beta$) functional relation than a $\sqrt{\delta^2+\beta^2}$ functional relation. We also observed that the Born approximation has a larger relative error for TM than for TE polarization. As any experimental measurement has a given level of uncertainty (noise) in the real diffraction pattern captured by the metrology apparatus, one can use these simulation results to determine the region of validity of the Born approximation for any particular experiment. For instance, given a relative noise level of 10^-3 we may conclude that the Born approximation can be safely used for materials where the approximation error is less than 10^-3. In the X-ray regime, this condition will be satisfied by most materials, using only the first Born approximation.

A simulation on the same structure, using extreme ultra-violet (EUV) illumination having a wavelength $\lambda=5$ nm was performed and compared with a reference has been computed with rigorous FMM with 501 harmonics (N=250). For a given contrast, the error is actually smaller than in the X-ray regime. However, taking into account that most materials have a much higher contrast in the EUV regime than in the x-ray regime, the Born approximation should be used with caution at this wavelength. Note, that that the conditions of validity are closely linked to the specific structure being modeled. The area of validity of the Born approximation in ($\delta$, $\beta$) space increases as the size of the scatterer (contrast features 604) decreases relative to the wavelength. This can be understood intuitively, as a very small scatterer inevitably results in a smaller difference between the true total field and the background field that is used as an approximation for it. In any case, it may be noted that the accuracy of the approximation can be increased by applying second and higher order Born approximations in the manner described above, and illustrated in FIG. 7. Criteria can be established by which the appropriate order of approximation is determined either in advance, or by calculation based on of the results of the iterations.

In FIG. 8 CPU time (vertical axis, log scale) is plotted against the number of harmonics N (horizontal axis, log scale). The graph confirms the cubic complexity of the rigorous FMM and the linear complexity of the Fourier modal method in Born approximation. Of course, any real application includes additional calculations for setup and communication. These complexities are therefore attained asymptotically, i.e. for a sufficiently large N. We conclude that in cases where the Born approximation is applicable, it can lead to a tremendous reduction of computational costs. For instance, for N=256 one-sided harmonics, the method uses harmonics ranging from $-N$ to N, so that the total number of harmonics calculated is 2N+1=513. Clearly the CPU time is reduced by almost three orders of magnitude, and this factor increases for larger N. We note that in the first Born approximation all matrices are diagonal (except $E_l$, which does not appear in a product with the unknown solution). Accordingly, there is no coupling between modes, and adding higher harmonics does not alter (improve) the reflection/transmission coefficients corresponding to lower harmonics. In other words, the number of harmonics that need to be used in the FMM in first Born approximation is purely determined by the set of orders that can be detected within the numerical aperture of the sensor (306, FIG. 3) and not by accuracy considerations.

As mentioned, T-SAXS metrology is only one example application in which the modal method with Born approximation may beneficially be applied. Furthermore, within the technique of T-SAXS variations can be envisaged, including variations with a conical mount (non-zero azimuth angle). In addition, inspection of both man-made and natural target structures using the disclosed simulation techniques can be performed using radiation in reflective modes, not only transmissive modes.

FIG. 9 illustrates schematically an apparatus 900 for performing High-resolution lensless imaging using EUV radiation reflected from the target structure. More detail of this apparatus and method is provided in pending patent application EP15180807.8, mentioned in the introduction. The context of that application is hereby incorporated by reference. Lensless imaging can be performed by calculating the image from one or more recorded diffraction patterns, without a physical imaging system. A product structure 907 is formed with defects that are to be detected by the lensless imaging. A spot (S) of EUV radiation which is at least partially coherent is provided on the product structure while a detector 908 captures at least one diffraction pattern formed by the radiation after scattering by a product structure 907. At least one synthetic image (616) of the product structure is calculated from the captured image data by a processor 910.

Processor 910 may implement a method of the type disclosed above to simulate interaction of the EUV radiation with the target structure. The method may be used in a reconstruction context as illustrated in FIG. 4, or in some other context. For defect metrology, the synthetic image may be compared with reference data that describes a nominal product structure. In one embodiment, the lensless imaging technique used is ptychography. A number of diffraction patterns are obtained using a series of overlapping spots (S, S'), and the synthetic image is calculated using the diffraction patterns and knowledge of the relative displacement. The EUV radiation may have wavelengths in the range 5 to 50 nm, close to dimensions of the structures of interest. The radiation source 912 may be for example a higher harmonic generator (HHG) source based on a laser and HHG cell.

FIG. 10 illustrates schematically another metrology apparatus based on reflection of x-ray and/or EUV radiation generated using an inverse Compton scattering source. More detail of this apparatus and method is provided in pending patent application EP15180740.1, mentioned in the introduction. The context of that application is hereby incorporated by reference. Using the inverse Compton scattering source, X-ray, EUV, UV and VIS radiation can be generated with high brightness and rapid frequency switching. In the drawing, a target structure (T) made by lithography or used in lithography is inspected by irradiating the structure at least a first time with EUV radiation 1004 generated by inverse Compton scattering source 1030. In this type of source a high energy electron beam interacts with a laser beam in a cavity to generate output radiation at x-ray or longer wavelengths. Radiation 1008 scattered by the target structure in reflection or transmission is detected by detector 1012 and properties of the target structure are calculated by a processor 1040 based on the detected scattered radiation.

Processor 1040 may implement a method of the type disclosed above to simulate interaction of the EUV radiation with the target structure. The method may be used in a reconstruction context as illustrated in FIG. 4, or in some other context. The radiation may have a first wavelength in the EUV range of 0.1 nm to 125 nm. Using the same source and controlling an electron energy, the structure may be irradiated multiple times with different wavelengths within the EUV range, and/or with shorter (x-ray) wavelengths and/or with longer (UV, visible) wavelengths. By rapid switching of electron energy in the inverse Compton scattering source (330), irradiation at different wavelengths can be performed several times per second. Performing reconstruction with information from different wavelengths can resolve ambiguities that would otherwise be present in solving the Maxwell equations.

Also to improve accuracy, measurements made with two or more types of apparatus can be obtained in a variety of hybrid techniques. More details of the metrology apparatuses can be found in the patent applications referred to above. It will be understood that they are only examples of the many types of apparatuses and methods in which the techniques disclosed herein may be applied. Any or all of these types of apparatuses can be used in a given application, whether for semiconductor manufacturing or other purposes.

CONCLUSIONS

In conclusion, the present disclosure provides modified techniques for use in reconstruction type metrology, and also other applications where it is useful to be able to simulate interaction of radiation with a mathematical model of a structure. In particular in the case of short wavelength radiation in the EUV and x-ray bands, the use of a modal method in Born approximation can lead to very significant savings in computation, with well-defined accuracy.

An embodiment of the invention may be implemented using a computer program containing one or more sequences of machine-readable instructions describing methods of controlling the lithographic apparatus using height map data as described above. This computer program may be executed for example within the control unit LACU 206 of FIG. 1, the additional metrology apparatus 240 and 244, the supervisory control system 238 or some other controller. There may also be provided a data storage medium (e.g., semiconductor memory, magnetic or optical disk) having such a computer program stored therein. The storage may be of non-transitory type.

Further embodiments according to the invention are provided in below numbered clauses:

1. A method of simulating interaction of radiation with a structure, the method including the steps of:
(a) defining a layered structure model to represent the structure in a two- or three-dimensional model space, the structure model defining for each layer of the structure a homogeneous background permittivity and for at least one layer a non-homogeneous contrast permittivity; and
(b) using the structure model in a modal method to simulate interaction of radiation with the structure, a total field being calculated in terms of a background field and a contrast field, the background field within each layer being independent of the contrast permittivity.
wherein step (b) uses Maxwell's equation in a Born approximation, whereby a product of the contrast permittivity and the total field is approximated by a product of the contrast permittivity and the background field.
2. A method according to clause 1 wherein said structure model defines a unit cell of a structure that is periodic in one or more directions.
3. A method according to clause 1 or 2 wherein said modal method is constructed so as to have a system matrix Q that is a diagonal matrix.
4. A method according to clause 1, 2 or 3 wherein said structure model defines said structure as a series of layers in a first direction, the modal method being performed by solving the Maxwell equation analytically in said first direction within each layer and connecting the solutions obtained for the series of layers to obtain a solution for the structure as a whole.
5. A method according to any preceding clause wherein said modal method is performed using order N modes and a solution of said Maxwell's equation in the Born approximation requires order N calculations in at least a first iteration.
6. A method according to any of clauses 1 to 5 wherein in step (b) said modal method is repeated one or more times, each time using a product of the contrast permittivity and a total field calculated approximately the previous time, as an approximation for the product of the contrast permittivity and the total field, thereby to implement a second order or higher order Born approximation of the Maxwell equation.
7. A method according to clause 6 wherein said modal method is performed using order N modes and a solution of said Maxwell's equation in the Born approximation requires order N log N calculations when repeated.
8. A method according to any preceding clause wherein the simulated radiation has a wavelength shorter than 100 nm.

9. A method according to any preceding clause wherein the simulated radiation has a wavelength in the range 0.01 nm to 10 nm.

10. A method according to any preceding clause wherein said modal method is a Fourier modal method.

11. A method according to any preceding clause wherein the structure model represents part of a semiconductor device made by lithography.

12. A method of determining parameters of a structure, the method comprising performing the steps (a) and (b) of a method according to any of clauses 1 to 11 to simulate interaction of radiation with the structure, and (c) repeating step (b) while varying parameters of the structure model.

13. A method according to clause 12 wherein step (c) comprises:

(c1) comparing the interaction simulated in step (b) with a real interaction observed in a metrology apparatus with said target structure;

(c2) varying one or more parameters of the structure model based on the result of the comparison; and (c3) repeating step (b) using the varied parameters, and wherein the method further comprises:

(d) after a number of iterations of step (c) reporting parameters of the structure model as a measurement of parameters of the target structure.

14. A method according to clause 12 or 14 wherein the simulated interaction and the real interaction use radiation having a wavelength shorter than 100 nm.

15. A method according to clause 12, 13 or 14 wherein the simulated interaction and the real interaction use radiation having a wavelength in the range 0.1 nm to 10 nm.

16. A method according to clause 12, 13 or 14 wherein the simulated interaction and the real interaction use radiation having a wavelength in the range 0.01 nm to 1.0 nm.

17. A method according to any of clauses 12 to 16 wherein the simulated interaction and the real interaction comprise transmission of radiation through the structure.

18. A method according to clause 17 wherein said metrology apparatus is a transmission small-angle x-ray scatterometer.

19. A method according to any of clauses 12 to 17 wherein the simulated interaction and the real interaction comprise reflection of radiation by the structure.

20. A processing apparatus for use in simulating interaction of radiation with a structure, the processing apparatus comprising:

storage for a layered structure model to represent the structure in a two- or three-dimensional model space, the structure model defining for each layer of the structure a homogeneous background permittivity and for at least one layer a non-homogeneous contrast permittivity; and a processor for using the structure model in a modal method to simulate interaction of radiation with the structure, a total field being calculated in terms of a background field and a contrast field, the background field within each layer being independent of the contrast permittivity.

wherein the processor is arranged to use Maxwell's equation in a Born approximation, whereby a product of the contrast permittivity and the total field is approximated by a product of the contrast permittivity and the background field.

21. A processing apparatus according to clause 20 wherein the process is arranged to perform said modal method using a system matrix Q that is a diagonal matrix.

22. A processing apparatus according to clause 20 or 21 wherein said structure model defines said structure as a series of layers in a first direction, the modal method being performed by solving the Maxwell equation analytically in said first direction within each layer and connecting the solutions obtained for the series of layers to obtain a solution for the structure as a whole.

23. A processing apparatus according to any of clauses 20 to 22 wherein the processor is arranged to repeated said modal method one or more times, each time using a product of the contrast permittivity and a total field calculated approximately the previous time, as an approximation for the product of the contrast permittivity and the total field, thereby to implement a second order or higher order Born approximation of the Maxwell equation.

24. A processing apparatus according to any of clauses 20 to 23 wherein said modal method is a Fourier modal method.

25. An apparatus for determining parameters of a structure, the apparatus comprising a processing apparatus according to any of clauses 20 to 24 for simulating interaction of radiation with the structure, and repeating operation of the processor while varying parameters of the structure model.

26. An apparatus according to clause 25 wherein the apparatus is arranged to repeat operation of the processor by:

comparing the interaction simulated in step (b) with a real interaction observed in a metrology apparatus with said target structure;

varying one or more parameters of the structure model based on the result of the comparison;

repeating operation of the processor using the varied parameters; and after a number of operations of the processor to report parameters of the structure model as a measurement of parameters of the target structure.

27. A metrology apparatus for use in determining parameters of a structure, the metrology apparatus comprising:

an irradiation system for generating a beam of radiation;

a substrate support operable with the irradiation system for irradiating a structure formed on the substrate with radiation;

a detection system for detecting radiation after interaction with the structure; and an apparatus according to clause 25 or 26 arranged to determine a property of the structure based on the detected radiation.

28. A device manufacturing method comprising:

transferring a pattern from a patterning device onto a substrate using a lithographic process, the pattern defining at least one structure;

measuring one or more properties of the structure to determine a value for one or more parameters of the lithographic process; and applying a correction in subsequent operations of the lithographic process in accordance with the measured property, wherein the step of measuring the properties of the structure includes determining a property by a method according to any of clauses 12 to 19.

29. A lithographic system comprising a lithographic apparatus in combination with a metrology apparatus according to clause 28.

30. A computer program product comprising machine readable instructions for causing a processor to perform a method according to any of clauses 1 to 19.

31. A computer program product comprising machine readable instructions for causing a processor to perform as the processor in an apparatus according to any of clauses 20 to 27.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 0.1 to 125 nm), as well as x-radiation (0.01 to 1 nm) and particle beams, such as ion beams or electron beams.

The terms "radiation" and "beam" used herein further encompass other forms of radiation including acoustic (sound) radiation. Phenomena of scattering and diffraction arise also in sound, and similar calculations can be performed for reconstruction of unknown structures by acoustic scattering.

The term "lens", where the context allows, may refer to any one or combination of various types of optical components, including refractive, reflective, magnetic, electromagnetic and electrostatic optical components.

The breadth and scope of the present invention should not be limited by any of the above-described exemplary embodiments, but should be defined only in accordance with the following claims and their equivalents.

REFERENCES (NON-PATENT LITERATURE)

(1) P. Lemaillet et al, "Intercomparison between optical and x-ray scatterometry measurements of FinFET structures" Metrology, Inspection, and Process Control for Microlithography XXVII, Proc. of SPIE Vol. 8681, 2013
(2) Ronald L. Jones, et al. "Small angle x-ray scattering for sub-100 nm pattern", Appl. Phys. Lett. 83, 4059 (2003)
(3) J. Li, X. Wang, and T. Wang, "ON THE VALIDITY OF BORN APPROXIMATION". Progress In Electromagnetics Research, Vol. 107, 219-237, 2010
(4) S. K. Sinha, E. B. Sirota, S. Garoff and H. B. Stanley, "x-ray and neutron scattering from rough surfaces", Phys. Rev. B 38, 2297-2311 (1988)
(5) Van den Berg, P. M., "Iterative computational techniques in scattering based upon the integrated square error criterion," IEEE Transactions on Antennas and Propagation, Vol. 32, No. 10, 1063-1071, 1984
(6) Trattner, S., M. Feigin, H. Greenspan, and N. Sochen, "Validity criterion for the Born approximation convergence in microscopy imaging," J. Opt. Soc. Am. A, Vol. 26, No. 5, 1147-1156, 2009.
(7) Pisarenco, M., Maubach, J. M. L., Setija, I. D., Mattheij, R. M. M., "Aperiodic Fourier modal method in contrast-field formulation for simulation of scattering from finite structures. Journal of the Optical Society of America. A, Optics, Image Science and Vision, 27(11), 2423-2431, 2010
(8) Pisarenco, M., Maubach, J. M. L., Setija, I. D., Mattheij, R. M. M., "Modified S-matrix algorithm for the aperiodic Fourier modal method in contrast-field formulation,", J. Opt. Soc. Am. A 28, 1364-1371 (2011).

The invention claimed is:

1. A method for determining changes to a lithographic exposure process used to form a structure on a substrate or expose one or more subsequent substrates, the method comprising:
defining a layered structure model to represent the structure on the substrate in a two- or three-dimensional model space, the structure model defining for each layer of the structure a homogeneous background permittivity and for at least one layer a non-homogeneous contrast permittivity; and
using the layered structure model in a modal method to simulate interaction of radiation with the structure, a total field being calculated in terms of a background field and a contrast field, the background field within each layer being independent of the non-homogeneous contrast permittivity, wherein the simulated interaction uses Maxwell's equation in a Born approximation, whereby a product of the non-homogeneous contrast permittivity and the total field is approximated by a product of the non-homogeneous contrast permittivity and the background field;
comparing the interaction simulated with results of a real interaction observed in a metrology apparatus with the structure to generate comparison results; and
storing the comparison results in a memory such that adjustments to exposure of subsequent substrates or reworking of the substrate with the structure can be done using the comparison results to improve yield.

2. The method of claim 1, wherein said structure model defines a unit cell of a structure that is periodic in one or more directions.

3. The method of claim 1, wherein said modal method is constructed so as to have a system matrix Q that is a diagonal matrix.

4. The method of claim 1, wherein said structure model defines said structure as a series of layers in a first direction, the modal method being performed by solving the Maxwell equation analytically in said first direction within each layer and connecting the solutions obtained for the series of layers to obtain a solution for the structure as a whole.

5. The method of claim 1, wherein said modal method is performed using order N modes and a solution of said Maxwell's equation in the Born approximation requires order N calculations in at least a first iteration.

6. The method of claim 1, wherein the simulated interaction is repeated one or more times, each time using a product of the non-homogeneous contrast permittivity and a total field calculated approximately the previous time, as an approximation for the product of the non-homogeneous contrast permittivity and the total field, thereby to implement a second order or higher order Born approximation of the Maxwell equation.

7. A processing apparatus for determining changes to a lithographic exposure process used to form a structure on a substrate or expose one or more subsequent substrates, the processing apparatus comprising:
a non-transitory computer-readable storage device configured to store a layered structure model to represent the structure on the substrate in a two- or three-dimensional model space, the structure model defining for each layer of the structure a homogeneous background permittivity and for at least one layer a non-homogeneous contrast permittivity; and
a processor configured to use the structure model in a modal method to simulate interaction of radiation with the structure, a total field being calculated in terms of a background field and a contrast field, the background field within each layer being independent of the non-homogeneous contrast permittivity,
wherein the processor is configured to use Maxwell's equation in a Born approximation, whereby a product of the non-homogeneous contrast permittivity and the total field is approximated by a product of the non-homogeneous contrast permittivity and the background field,
wherein the processor is configured to compare the interaction simulated with results of a real interaction observed in a metrology apparatus with the structure to generate comparison results, and
wherein the processor is configured to store the comparison results in a memory such that adjustments to exposure of subsequent substrates or reworking of the substrate with the structure can be done using the comparison results to improve yield.

8. The processing apparatus of claim 7, wherein the processor is configured to perform said modal method using a system matrix Q that is a diagonal matrix.

9. The processing apparatus of claim 7, wherein said structure model defines said structure as a series of layers in a first direction, and wherein the processor is configured to solve the Maxwell equation analytically in said first direction within each layer and connecting the solutions obtained for the series of layers to obtain a solution for the structure as a whole.

10. The processing apparatus of claim 7, wherein the processor is configured to repeated said modal method one or more times, each time using a product of the non-homogeneous contrast permittivity and a total field calculated approximately the previous time, as an approximation for the product of the non-homogeneous contrast permittivity and the total field, thereby to implement a second order or higher order Born approximation of the Maxwell equation.

11. The processing apparatus of claim 7, wherein the apparatus is configured to repeat operation of the processor by:
varying one or more parameters of the structure model based on the result of the comparison;
repeating operation of the processor using the varied parameters; and
after a number of operations of the processor to report parameters of the structure model as a measurement of parameters of the target structure.

12. A metrology apparatus for use in determining parameters of a structure, the metrology apparatus comprising:
an irradiation system for generating a beam of radiation;
a substrate support operable with the irradiation system for irradiating a structure formed on the substrate with radiation;
a detection system for detecting radiation after interaction with the structure; and
an apparatus configured to determine a property of the structure based on the detected radiation, the apparatus comprising:
storage for a layered structure model to represent the structure on the substrate in a two- or three-dimensional model space, the structure model defining for each layer of the structure a homogeneous background permittivity and for at least one layer a non-homogeneous contrast permittivity; and
a processor configured to use the structure model in a modal method to simulate interaction of radiation with the structure, a total field being calculated in terms of a background field and a contrast field, the background field within each layer being independent of the non-homogeneous contrast permittivity, and
wherein the processor is configured to use Maxwell's equation in a Born approximation, whereby a product of the non-homogeneous contrast permittivity and the total field is approximated by a product of the non-homogeneous contrast permittivity and the background field, and
wherein the processor is configured to compare the interaction simulated with results of a real interaction observed in a metrology apparatus with the structure to generate comparison results, and
wherein the processor is configured store the comparison results in a memory such that adjustments to exposure of subsequent substrates or reworking of the substrate with the structure can be done using the comparison results to improve yield.

13. A device manufacturing method comprising:
transferring a pattern from a patterning device onto a substrate using a lithographic process, the pattern defining at least one structure;
measuring one or more properties of the structure to determine a value for one or more parameters of the lithographic process; and
applying a correction in subsequent operations of the lithographic process in accordance with the measured property,
wherein the step of measuring the properties of the structure includes determining a property by:
defining a layered structure model to represent the structure on the substrate in a two- or three-dimensional model space, the layered structure model defining for each layer of the structure a homogeneous background permittivity and for at least one layer a non-homogeneous contrast permittivity; and
using the structure model in a modal method to simulate interaction of radiation with the structure, a total field being calculated in terms of a background field and a contrast field, the background field within each layer being independent of the non-homogeneous contrast permittivity, and
repeating the simulated interaction while varying parameters of the structure model;
comparing the interaction simulated with results of a real interaction observed in a metrology apparatus with the structure to generate comparison results; and
storing the comparison results in a memory such that adjustments to exposure of subsequent substrates or reworking of the substrate with the structure can be done using the comparison results to improve yield.

* * * * *